United States Patent
Visentin et al.

(10) Patent No.: US 10,202,633 B2
(45) Date of Patent: *Feb. 12, 2019

(54) POLYPEPTIDE SUBSTRATE FOR THE DETECTION OF VON WILLIEBRAND FACTOR CLEAVING PROTEASE ADAMTS13

(71) Applicant: IMMUCOR GTI DIAGNOSTICS, INC., Waukesha, WI (US)

(72) Inventors: Gian Paolo Visentin, Waukesha, WI (US); Suzette C. Chance, Richfield, WI (US); Elizabeth Wuitschick, Wauwatosa, WI (US)

(73) Assignee: IMMUCOR GTI DIAGNOSTICS, INC., Waukesha, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/369,235

(22) Filed: Dec. 5, 2016

(65) Prior Publication Data

US 2017/0145471 A1    May 25, 2017

Related U.S. Application Data

(63) Continuation of application No. 14/357,988, filed as application No. PCT/US2012/064526 on Nov. 9, 2012, now Pat. No. 9,513,290.

(60) Provisional application No. 61/558,927, filed on Nov. 11, 2011.

(51) Int. Cl.
*C12Q 1/37* (2006.01)
*C07K 14/755* (2006.01)
*G01N 33/573* (2006.01)

(52) U.S. Cl.
CPC .............. *C12Q 1/37* (2013.01); *C07K 14/755* (2013.01); *G01N 33/573* (2013.01); *C07K 2319/60* (2013.01); *G01N 2333/755* (2013.01); *G01N 2333/96486* (2013.01)

(58) Field of Classification Search
None
See application file for complete search history.

(56) References Cited

U.S. PATENT DOCUMENTS

2013/0023004 A1    1/2013  Sadler

OTHER PUBLICATIONS

Gao et al., "Extensive contacts between ADAMTS13 exosites and von Willebrand factor domain A2 contribute to substrate specificity", Blood. Sep. 1, 2008; 112(5): 1713-1719. doi: 10.1182/blood-2008-04-148759.*
Mar. 9, 2016 Examination Report issued in European Patent Application No. 12 788 406.2.
Koichi Kokame et al, "FRETS-VWF73, a first fluorogenic substrate for ADAMTS13 assay", British Journal of Haematology, (Mar. 14, 2005), vol. 129, No. 1, doi:10.1111/j.1365-21412005.05420.x, ISSN 0007-1048, p. 33-100 XP055052565.
Kannayakanahalli M Dayananda et al, "*Escherichia coli*-derived von Willebrand factor-A2 domain fluorescence/Forster resonance energy transfer proteins that quantify ADAMTS13 activity", Analytical Biochemistry, Academic Press Inc, New York, vol. 410, No. 2, doi:10.1016/J.AB.2010.12.005, ISSN 0003-2697, (Dec. 6, 2010), p. 206-213, (Dec. 10, 2010), XP028146262.
Raife et al., "Leukocyte proteases cleave vonWillebrand factor at or near theADAMTS13 cleavage site", Blood, 2009, 114(8): 1666-1674.
Airaksinen et al., Nucleic Acids Res 26:576-581, 1998.
Folz et al., J. Biol. Chem. 263:2070-2078, 1988.

* cited by examiner

*Primary Examiner* — Suzanne M Noakes
(74) *Attorney, Agent, or Firm* — Mintz Levin Cohn Ferris Glovsky and Popeo, P.C.

(57) ABSTRACT

In a first aspect, there is provided an isolated polypeptide substrate for a disintegrin-like and metallopeptidase with thrombospondin type-1 motif, 13 (ADAMTS13) that is from 45 to 70 amino acids in length and has an amino acid sequence that is substantially similar to part of the von Willebrand factor A2 domain sequence set forth in SEQ ID NO: 2, with one or more of the following modifications: (i) the amino acid corresponding to position 1599 of SEQ ID NO: 2 is mutated from Q to K; (ii) the amino acid corresponding to position 1610 of SEQ ID NO: 2 is mutated from N to C; and (iii) the amino acids corresponding to Q1624 to R1641 of SEQ ID NO: 2 are deleted. In another aspect, there is provided an ADAMTS13 polypeptide substrate that is from 50 to 75 amino acids in length and has an amino acid sequence that is substantially similar to part of the von Willebrand factor A2 domain sequence set forth in SEQ ID NO: 2, with one or more of the following modifications: (i) the amino acid corresponding to position 1599 of SEQ ID NO: 2 is mutated from Q to K; (ii) the amino acid corresponding to position 1610 of SEQ ID NO: 2 is mutated from N to C; (iii) the amino acid corresponding to position 1629 of SEQ ID NO: 2 is mutated from G to E; and (iv) the amino acids corresponding to G1631 to R1641 of SEQ ID NO: 2 are deleted.

20 Claims, 5 Drawing Sheets

Specification includes a Sequence Listing.

FIGURE 1

```
                                                            1498
                                                              DVA
       1510       1520       1530       1540       1550       1560
   FVLECSDKIC EADFNRSKEF MEEVIQRMDV CQDSIHVTVL QYSYMVTVEY PFSEAQSKGD 1570       1580       1590       1600       1610       1620
   ILQRVREIRY QGGNRTNTGL ALRYLSDHSF LVSQGDREQA PNLVYMVTGN PASDEIKRLP 1630       1640       1650       1660       1668
   GDIQVVPIGV GPNANVQELE RIGWFNAPIL IQDFETLPRE APDLVLQR
```

FIGURE 2

▼ = Y1605-M1606 (ADAMTS13 cleavage site)
NH2-DREKAPNLVYM/TGCPASDEIKRLPGDIQVVPIEVIGWPNAPILIQDFETLPPEAPDLVLQR-COOH
 1  4      10   15                  34                            62

SEQUENCE LISTING

<160> NUMBER OF SEQ ID NOS: 8

<210> SEQ ID NO 1
<211> LENGTH: 62
<212> TYPE: PRT
<213> ORGANISM: Artificial Sequence
<220> FEATURE:
<223> OTHER INFORMATION: Description of Artificial Sequence: Synthetic polymer polypeptide

<400> SEQUENCE: 1

Asp Arg Glu Lys Ala Pro Asn Leu Val Tyr Met Val Thr Gly Cys Pro
1               5                   10                  15

Ala Ser Asp Glu Ile Lys Arg Leu Pro Gly Asp Ile Gln Val Val Pro
            20                  25                  30

Ile Glu Val Ile Gly Trp Pro Asn Ala Pro Ile Leu Ile Gln Asp Phe
        35                  40                  45

Glu Thr Leu Pro Arg Glu Ala Pro Asp Leu Val Leu Gln Arg
    50                  55                  60

<210> SEQ ID NO 2
<211> LENGTH: 2813
<212> TYPE: PRT
<213> ORGANISM: Homo sapiens
<220> FEATURE:
<223> OTHER INFORMATION: Human von Willebrand factor precursor

<400> SEQUENCE: 2

```
Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205

Ser Cys Asn Ile Ser Ser Gly Glu Met Gln Lys Gly Leu Trp Glu Gln
    210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
        275                 280                 285

Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
        355                 360                 365

Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415
```

-continued

```
Asp Cys Gln Asp His Ser Phe Ser Ile Val Glu Thr Val Gln Cys
                420                 425                 430

Ala Asp Asp Arg Asp Ala Val Cys Thr Arg Ser Val Thr Val Arg Leu
435                 440                 445

Pro Gly Leu His Asn Ser Leu Val Lys Leu Lys His Gly Ala Gly Val
    450                 455                 460

Ala Met Asp Gly Gln Asp Val Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
    515                 520                 525

Gly Asn Gln Gly Asp Asp Phe Leu Thr Pro Ser Gly Leu Ala Glu Pro
    530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
                595                 600                 605

Arg Tyr Asp Val Cys Ser Cys Ser Asp Gly Arg Glu Cys Leu Cys Gly
    610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
                645                 650                 655

Val Tyr Leu Gln Cys Gly Thr Pro Cys Asn Leu Thr Cys Arg Ser Leu
            660                 665                 670

Ser Tyr Pro Asp Glu Glu Cys Asn Glu Ala Cys Leu Glu Gly Cys Phe
    675                 680                 685

Cys Pro Pro Gly Leu Tyr Met Asp Glu Arg Gly Asp Cys Val Pro Lys
    690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
    755                 760                 765

Pro Pro Met Val Lys Leu Val Cys Pro Ala Asp Asn Leu Arg Ala Glu
    770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
            820                 825                 830
```

```
Gly Lys Glu Tyr Ala Pro Gly Glu Thr Val Lys Ile Gly Cys Asn Thr
        835                 840                 845
Cys Val Cys Gln Asp Arg Lys Trp Asn Cys Thr Asp His Val Cys Asp
850                 855                 860
Ala Thr Cys Ser Thr Ile Gly Met Ala His Tyr Leu Thr Phe Asp Gly
865                 870                 875                 880
Leu Lys Tyr Leu Phe Pro Gly Glu Cys Gln Tyr Val Leu Val Gln Asp
                885                 890                 895
Tyr Cys Gly Ser Asn Pro Gly Thr Phe Arg Ile Leu Val Gly Asn Lys
            900                 905                 910
Gly Cys Ser His Pro Ser Val Lys Cys Lys Arg Val Thr Ile Leu
        915                 920                 925
Val Glu Gly Gly Glu Ile Glu Leu Phe Asp Gly Glu Val Asn Val Lys
        930                 935                 940
Arg Pro Met Lys Asp Glu Thr His Phe Glu Val Val Glu Ser Gly Arg
945                 950                 955                 960
Tyr Ile Ile Leu Leu Leu Gly Lys Ala Leu Ser Val Val Trp Asp Arg
                965                 970                 975
His Leu Ser Ile Ser Val Val Leu Lys Gln Thr Tyr Gln Glu Lys Val
            980                 985                 990
Cys Gly Leu Cys Gly Asn Phe Asp  Gly Ile Gln Asn Asn  Asp Leu Thr
        995                 1000                1005
Ser Ser  Asn Leu Gln Val Glu  Glu Asp Pro Val Asp  Phe Gly Asn
    1010                1015                1020
Ser Trp  Lys Val Ser Ser Gln  Cys Ala Asp Thr Arg  Lys Val Pro
    1025                1030                1035
Leu Asp  Ser Ser Pro Ala Thr  Cys His Asn Asn Ile  Met Lys Gln
    1040                1045                1050
Thr Met  Val Asp Ser Ser Cys  Arg Ile Leu Thr Ser  Asp Val Phe
    1055                1060                1065
Gln Asp  Cys Asn Lys Leu Val  Asp Pro Glu Pro Tyr  Leu Asp Val
    1070                1075                1080
Cys Ile  Tyr Asp Thr Cys Ser  Cys Glu Ser Ile Gly  Asp Cys Ala
    1085                1090                1095
Cys Phe  Cys Asp Thr Ile Ala  Ala Tyr Ala His Val  Cys Ala Gln
    1100                1105                1110
His Gly  Lys Val Val Thr Trp  Arg Thr Ala Thr Leu  Cys Pro Gln
    1115                1120                1125
Ser Cys  Glu Glu Arg Asn Leu  Arg Glu Asn Gly Tyr  Glu Cys Glu
    1130                1135                1140
Trp Arg  Tyr Asn Ser Cys Ala  Pro Ala Cys Gln Val  Thr Cys Gln
    1145                1150                1155
His Pro  Glu Pro Leu Ala Cys  Pro Val Gln Cys Val  Glu Gly Cys
    1160                1165                1170
His Ala  His Cys Pro Pro Gly  Lys Ile Leu Asp Glu  Leu Leu Gln
    1175                1180                1185
Thr Cys  Val Asp Pro Glu Asp  Cys Pro Val Cys Glu  Val Ala Gly
    1190                1195                1200
Arg Arg  Phe Ala Ser Gly Lys  Lys Val Thr Leu Asn  Pro Ser Asp
    1205                1210                1215
Pro Glu  His Cys Gln Ile Cys  His Cys Asp Val Val  Asn Leu Thr
    1220                1225                1230
```

```
Cys Glu Ala Cys Gln Glu Pro Gly Gly Leu Val Val Pro Pro Thr
1235                1240                1245

Asp Ala Pro Val Ser Pro Thr Thr Leu Tyr Val Glu Asp Ile Ser
1250                1255                1260

Glu Pro Pro Leu His Asp Phe Tyr Cys Ser Arg Leu Leu Asp Leu
1265                1270                1275

Val Phe Leu Leu Asp Gly Ser Ser Arg Leu Ser Glu Ala Glu Phe
1280                1285                1290

Glu Val Leu Lys Ala Phe Val Val Asp Met Met Glu Arg Leu Arg
1295                1300                1305

Ile Ser Gln Lys Trp Val Arg Val Ala Val Val Glu Tyr His Asp
1310                1315                1320

Gly Ser His Ala Tyr Ile Gly Leu Lys Asp Arg Lys Arg Pro Ser
1325                1330                1335

Glu Leu Arg Arg Ile Ala Ser Gln Val Lys Tyr Ala Gly Ser Gln
1340                1345                1350

Val Ala Ser Thr Ser Glu Val Leu Lys Tyr Thr Leu Phe Gln Ile
1355                1360                1365

Phe Ser Lys Ile Asp Arg Pro Glu Ala Ser Arg Ile Thr Leu Leu
1370                1375                1380

Leu Met Ala Ser Gln Glu Pro Gln Arg Met Ser Arg Asn Phe Val
1385                1390                1395

Arg Tyr Val Gln Gly Leu Lys Lys Lys Val Ile Val Ile Pro
1400                1405                1410

Val Gly Ile Gly Pro His Ala Asn Leu Lys Gln Ile Arg Leu Ile
1415                1420                1425

Glu Lys Gln Ala Pro Glu Asn Lys Ala Phe Val Leu Ser Ser Val
1430                1435                1440

Asp Glu Leu Glu Gln Gln Arg Asp Glu Ile Val Ser Tyr Leu Cys
1445                1450                1455

Asp Leu Ala Pro Glu Ala Pro Pro Pro Thr Leu Pro Pro Asp Met
1460                1465                1470

Ala Gln Val Thr Val Gly Pro Gly Leu Leu Gly Val Ser Thr Leu
1475                1480                1485

Gly Pro Lys Arg Asn Ser Met Val Leu Asp Val Ala Phe Val Leu
1490                1495                1500

Glu Gly Ser Asp Lys Ile Gly Glu Ala Asp Phe Asn Arg Ser Lys
1505                1510                1515

Glu Phe Met Glu Glu Val Ile Gln Arg Met Asp Val Gly Gln Asp
1520                1525                1530

Ser Ile His Val Thr Val Leu Gln Tyr Ser Tyr Met Val Thr Val
1535                1540                1545

Glu Tyr Pro Phe Ser Glu Ala Gln Ser Lys Gly Asp Ile Leu Gln
1550                1555                1560

Arg Val Arg Glu Ile Arg Tyr Gln Gly Gly Asn Arg Thr Asn Thr
1565                1570                1575

Gly Leu Ala Leu Arg Tyr Leu Ser Asp His Ser Phe Leu Val Ser
1580                1585                1590

Gln Gly Asp Arg Glu Gln Ala Pro Asn Leu Val Tyr Met Val Thr
1595                1600                1605

Gly Asn Pro Ala Ser Asp Glu Ile Lys Arg Leu Pro Gly Asp Ile
1610                1615                1620
```

-continued

Gln Val Val Pro Ile Gly Val Gly Pro Asn Ala Asn Val Gln Glu
1625                1630                1635

Leu Glu Arg Ile Gly Trp Pro Asn Ala Pro Ile Leu Ile Gln Asp
1640                1645                1650

Phe Glu Thr Leu Pro Arg Glu Ala Pro Asp Leu Val Leu Gln Arg
1655                1660                1665

Cys Cys Ser Gly Glu Gly Leu Gln Ile Pro Thr Leu Ser Pro Ala
1670                1675                1680

Pro Asp Cys Ser Gln Pro Leu Asp Val Ile Leu Leu Leu Asp Gly
1685                1690                1695

Ser Ser Ser Phe Pro Ala Ser Tyr Phe Asp Glu Met Lys Ser Phe
1700                1705                1710

Ala Lys Ala Phe Ile Ser Lys Ala Asn Ile Gly Pro Arg Leu Thr
1715                1720                1725

Gln Val Ser Val Leu Gln Tyr Gly Ser Ile Thr Thr Ile Asp Val
1730                1735                1740

Pro Trp Asn Val Val Pro Glu Lys Ala His Leu Leu Ser Leu Val
1745                1750                1755

Asp Val Met Gln Arg Glu Gly Gly Pro Ser Gln Ile Gly Asp Ala
1760                1765                1770

Leu Gly Phe Ala Val Arg Tyr Leu Thr Ser Glu Met His Gly Ala
1775                1780                1785

Arg Pro Gly Ala Ser Lys Ala Val Val Ile Leu Val Thr Asp Val
1790                1795                1800

Ser Val Asp Ser Val Asp Ala Ala Ala Asp Ala Ala Arg Ser Asn
1805                1810                1815

Arg Val Thr Val Phe Pro Ile Gly Ile Gly Asp Arg Tyr Asp Ala
1820                1825                1830

Ala Gln Leu Arg Ile Leu Ala Gly Pro Ala Gly Asp Ser Asn Val
1835                1840                1845

Val Lys Leu Gln Arg Ile Glu Asp Leu Pro Thr Met Val Thr Leu
1850                1855                1860

Gly Asn Ser Phe Leu His Lys Leu Cys Ser Gly Phe Val Arg Ile
1865                1870                1875

Cys Met Asp Glu Asp Gly Asn Glu Lys Arg Pro Gly Asp Val Trp
1880                1885                1890

Thr Leu Pro Asp Gln Cys His Thr Val Thr Cys Gln Pro Asp Gly
1895                1900                1905

Gln Thr Leu Leu Lys Ser His Arg Val Asn Cys Asp Arg Gly Leu
1910                1915                1920

Arg Pro Ser Cys Pro Asn Ser Gln Ser Pro Val Lys Val Glu Glu
1925                1930                1935

Thr Cys Gly Cys Arg Trp Thr Cys Pro Cys Val Cys Thr Gly Ser
1940                1945                1950

Ser Thr Arg His Ile Val Thr Phe Asp Gly Gln Asn Phe Lys Leu
1955                1960                1965

Thr Gly Ser Cys Ser Tyr Val Leu Phe Gln Asn Lys Glu Gln Asp
1970                1975                1980

Leu Glu Val Ile Leu His Asn Gly Ala Cys Ser Pro Gly Ala Arg
1985                1990                1995

Gln Gly Cys Met Lys Ser Ile Glu Val Lys His Ser Ala Leu Ser
2000                2005                2010

-continued

Val Glu Leu His Ser Asp Met Glu Val Thr Val Asn Gly Arg Leu
2015                2020                2025

Val Ser Val Pro Tyr Val Gly Gly Asn Met Glu Val Asn Val Tyr
2030                2035                2040

Gly Ala Ile Met His Glu Val Arg Phe Asn His Leu Gly His Ile
2045                2050                2055

Phe Thr Phe Thr Pro Gln Asn Asn Glu Phe Gln Leu Gln Leu Ser
2060                2065                2070

Pro Lys Thr Phe Ala Ser Lys Thr Tyr Gly Leu Cys Gly Ile Cys
2075                2080                2085

Asp Glu Asn Gly Ala Asn Asp Phe Met Leu Arg Asp Gly Thr Val
2090                2095                2100

Thr Thr Asp Trp Lys Thr Leu Val Gln Glu Trp Thr Val Gln Arg
2105                2110                2115

Pro Gly Gln Thr Cys Gln Pro Ile Leu Glu Glu Gln Cys Leu Val
2120                2125                2130

Pro Asp Ser Ser His Cys Gln Val Leu Leu Leu Pro Leu Phe Ala
2135                2140                2145

Glu Cys His Lys Val Leu Ala Pro Ala Thr Phe Tyr Ala Ile Cys
2150                2155                2160

Gln Gln Asp Ser Cys His Gln Glu Gln Val Cys Glu Val Ile Ala
2165                2170                2175

Ser Tyr Ala His Leu Cys Arg Thr Asn Gly Val Cys Val Asp Trp
2180                2185                2190

Arg Thr Pro Asp Phe Cys Ala Met Ser Cys Pro Pro Ser Leu Val
2195                2200                2205

Tyr Asn His Cys Glu His Gly Cys Pro Arg His Cys Asp Gly Asn
2210                2215                2220

Val Ser Ser Cys Gly Asp His Pro Ser Glu Gly Cys Phe Cys Pro
2225                2230                2235

Pro Asp Lys Val Met Leu Glu Gly Ser Cys Val Pro Glu Glu Ala
2240                2245                2250

Cys Thr Gln Cys Ile Gly Glu Asp Gly Val Gln His Gln Phe Leu
2255                2260                2265

Glu Ala Trp Val Pro Asp His Gln Pro Cys Gln Ile Cys Thr Cys
2270                2275                2280

Leu Ser Gly Arg Lys Val Asn Cys Thr Thr Gln Pro Cys Pro Thr
2285                2290                2295

Ala Lys Ala Pro Thr Cys Gly Leu Cys Glu Val Ala Arg Leu Arg
2300                2305                2310

Gln Asn Ala Asp Gln Cys Cys Pro Glu Tyr Glu Cys Val Cys Asp
2315                2320                2325

Pro Val Ser Cys Asp Leu Pro Pro Val Pro His Cys Glu Arg Gly
2330                2335                2340

Leu Gln Pro Thr Leu Thr Asn Pro Gly Glu Cys Arg Pro Asn Phe
2345                2350                2355

Thr Cys Ala Cys Arg Lys Glu Glu Cys Lys Arg Val Ser Pro Pro
2360                2365                2370

Ser Cys Pro Pro His Arg Leu Pro Thr Leu Arg Lys Thr Gln Cys
2375                2380                2385

Cys Asp Glu Tyr Glu Cys Ala Cys Asn Cys Val Asn Ser Thr Val
2390                2395                2400

-continued

Ser Cys Pro Leu Gly Tyr Leu Ala Ser Thr Ala Thr Asn Asp Cys
2405                2410                2415

Gly Cys Thr Thr Thr Thr Cys Leu Pro Asp Lys Val Cys Val His
2420                2425                2430

Arg Ser Thr Ile Tyr Pro Val Gly Gln Phe Trp Glu Glu Gly Cys
2435                2440                2445

Asp Val Cys Thr Cys Thr Asp Met Glu Asp Ala Val Met Gly Leu
2450                2455                2460

Arg Val Ala Gln Cys Ser Gln Lys Pro Cys Glu Asp Ser Cys Arg
2465                2470                2475

Ser Gly Phe Thr Tyr Val Leu His Glu Gly Glu Cys Cys Gly Arg
2480                2485                2490

Cys Leu Pro Ser Ala Cys Glu Val Val Thr Gly Ser Pro Arg Gly
2495                2500                2505

Asp Ser Gln Ser Ser Trp Lys Ser Val Gly Ser Gln Trp Ala Ser
2510                2515                2520

Pro Glu Asn Pro Cys Leu Ile Asn Glu Cys Val Arg Val Lys Glu
2525                2530                2535

Glu Val Phe Ile Gln Gln Arg Asn Val Ser Cys Pro Gln Leu Glu
2540                2545                2550

Val Pro Val Cys Pro Ser Gly Phe Gln Leu Ser Cys Lys Thr Ser
2555                2560                2565

Ala Cys Cys Pro Ser Cys Arg Cys Glu Arg Met Glu Ala Cys Met
2570                2575                2580

Leu Asn Gly Thr Val Ile Gly Pro Gly Lys Thr Val Met Ile Asp
2585                2590                2595

Val Cys Thr Thr Cys Arg Cys Met Val Gln Val Gly Val Ile Ser
2600                2605                2610

Gly Phe Lys Leu Glu Cys Arg Lys Thr Thr Cys Asn Pro Cys Pro
2615                2620                2625

Leu Gly Tyr Lys Glu Glu Asn Asn Thr Gly Glu Cys Cys Gly Arg
2630                2635                2640

Cys Leu Pro Thr Ala Cys Thr Ile Gln Leu Arg Gly Gly Gln Ile
2645                2650                2655

Met Thr Leu Lys Arg Asp Glu Thr Leu Gln Asp Gly Cys Asp Thr
2660                2665                2670

His Phe Cys Lys Val Asn Glu Arg Gly Glu Tyr Phe Trp Glu Lys
2675                2680                2685

Arg Val Thr Gly Cys Pro Pro Phe Asp Glu His Lys Cys Leu Ala
2690                2695                2700

Glu Gly Gly Lys Ile Met Lys Ile Pro Gly Thr Cys Cys Asp Thr
2705                2710                2715

Cys Glu Glu Pro Glu Cys Asn Asp Ile Thr Ala Arg Leu Gln Tyr
2720                2725                2730

Val Lys Val Gly Ser Cys Lys Ser Glu Val Glu Val Asp Ile His
2735                2740                2745

Tyr Cys Gln Gly Lys Cys Ala Ser Lys Ala Met Tyr Ser Ile Asp
2750                2755                2760

Ile Asn Asp Val Gln Asp Gln Cys Ser Cys Cys Ser Pro Thr Arg
2765                2770                2775

Thr Glu Pro Met Gln Val Ala Leu His Cys Thr Asn Gly Ser Val
2780                2785                2790

```
Val Tyr His Glu Val Leu Asn Ala Met Glu Cys Lys Cys Ser Pro
    2795                2800                2805

Arg Lys Cys Ser Lys
    2810

<210> SEQ ID NO 3
<211> LENGTH: 1427
<212> TYPE: PRT
<213> ORGANISM: Homo sapiens
<220> FEATURE:
<223> OTHER INFORMATION: A disintegrin and metalloproteinase with
      thrombospondin motifs 13 (Human) isoform 1

<400> SEQUENCE: 3

Met His Gln Arg His Pro Arg Ala Arg Cys Pro Pro Leu Cys Val Ala
1               5                   10                  15

Gly Ile Leu Ala Cys Gly Phe Leu Leu Gly Cys Trp Gly Pro Ser His
            20                  25                  30

Phe Gln Gln Ser Cys Leu Gln Ala Leu Glu Pro Gln Ala Val Ser Ser
        35                  40                  45

Tyr Leu Ser Pro Gly Ala Pro Leu Lys Gly Arg Pro Pro Ser Pro Gly
    50                  55                  60

Phe Gln Arg Gln Arg Gln Arg Gln Arg Arg Ala Ala Gly Gly Ile Leu
65                  70                  75                  80

His Leu Glu Leu Leu Val Ala Val Gly Pro Asp Val Phe Gln Ala His
                85                  90                  95

Gln Glu Asp Thr Glu Arg Tyr Val Leu Thr Asn Leu Asn Ile Gly Ala
            100                 105                 110

Glu Leu Leu Arg Asp Pro Ser Leu Gly Ala Gln Phe Arg Val His Leu
        115                 120                 125

Val Lys Met Val Ile Leu Thr Glu Pro Glu Gly Ala Pro Asn Ile Thr
    130                 135                 140

Ala Asn Leu Thr Ser Ser Leu Leu Ser Val Cys Gly Trp Ser Gln Thr
145                 150                 155                 160

Ile Asn Pro Glu Asp Asp Thr Asp Pro Gly His Ala Asp Leu Val Leu
                165                 170                 175

Tyr Ile Thr Arg Phe Asp Leu Glu Leu Pro Asp Gly Asn Arg Gln Val
            180                 185                 190

Arg Gly Val Thr Gln Leu Gly Gly Ala Cys Ser Pro Thr Trp Ser Cys
        195                 200                 205

Leu Ile Thr Glu Asp Thr Gly Phe Asp Leu Gly Val Thr Ile Ala His
    210                 215                 220

Glu Ile Gly His Ser Phe Gly Leu Glu His Asp Gly Ala Pro Gly Ser
225                 230                 235                 240

Gly Cys Gly Pro Ser Gly His Val Met Ala Ser Asp Gly Ala Ala Pro
                245                 250                 255

Arg Ala Gly Leu Ala Trp Ser Pro Cys Ser Arg Arg Gln Leu Leu Ser
            260                 265                 270

Leu Leu Ser Ala Gly Arg Ala Arg Cys Val Trp Asp Pro Pro Arg Pro
        275                 280                 285

Gln Pro Gly Ser Ala Gly His Pro Pro Asp Ala Gln Pro Gly Leu Tyr
    290                 295                 300

Tyr Ser Ala Asn Glu Gln Cys Arg Val Ala Phe Gly Pro Lys Ala Val
305                 310                 315                 320

Ala Cys Thr Phe Ala Arg Glu His Leu Asp Met Cys Gln Ala Leu Ser
                325                 330                 335
```

```
Cys His Thr Asp Pro Leu Asp Gln Ser Ser Cys Ser Arg Leu Leu Val
                340                 345                 350

Pro Leu Leu Asp Gly Thr Glu Cys Gly Val Glu Lys Trp Cys Ser Lys
            355                 360                 365

Gly Arg Cys Arg Ser Leu Val Glu Leu Thr Pro Ile Ala Ala Val His
        370                 375                 380

Gly Arg Trp Ser Ser Trp Gly Pro Arg Ser Pro Cys Ser Arg Ser Cys
385                 390                 395                 400

Gly Gly Gly Val Val Thr Arg Arg Gln Cys Asn Asn Pro Arg Pro
                405                 410                 415

Ala Phe Gly Gly Arg Ala Cys Val Gly Ala Asp Leu Gln Ala Glu Met
            420                 425                 430

Cys Asn Thr Gln Ala Cys Glu Lys Thr Gln Leu Glu Phe Met Ser Gln
        435                 440                 445

Gln Cys Ala Arg Thr Asp Gly Gln Pro Leu Arg Ser Ser Pro Gly Gly
    450                 455                 460

Ala Ser Phe Tyr His Trp Gly Ala Ala Val Pro His Ser Gln Gly Asp
465                 470                 475                 480

Ala Leu Cys Arg His Met Cys Arg Ala Ile Gly Glu Ser Phe Ile Met
                485                 490                 495

Lys Arg Gly Asp Ser Phe Leu Asp Gly Thr Arg Cys Met Pro Ser Gly
            500                 505                 510

Pro Arg Glu Asp Gly Thr Leu Ser Leu Cys Val Ser Gly Ser Cys Arg
        515                 520                 525

Thr Phe Gly Cys Asp Gly Arg Met Asp Ser Gln Gln Val Trp Asp Arg
    530                 535                 540

Cys Gln Val Cys Gly Gly Asp Asn Ser Thr Cys Ser Pro Arg Lys Gly
545                 550                 555                 560

Ser Phe Thr Ala Gly Arg Ala Arg Glu Tyr Val Thr Phe Leu Thr Val
                565                 570                 575

Thr Pro Asn Leu Thr Ser Val Tyr Ile Ala Asn His Arg Pro Leu Phe
            580                 585                 590

Thr His Leu Ala Val Arg Ile Gly Gly Arg Tyr Val Val Ala Gly Lys
        595                 600                 605

Met Ser Ile Ser Pro Asn Thr Thr Tyr Pro Ser Leu Leu Glu Asp Gly
    610                 615                 620

Arg Val Glu Tyr Arg Val Ala Leu Thr Glu Asp Arg Leu Pro Arg Leu
625                 630                 635                 640

Glu Glu Ile Arg Ile Trp Gly Pro Leu Gln Glu Asp Ala Asp Ile Gln
                645                 650                 655

Val Tyr Arg Arg Tyr Gly Glu Glu Tyr Gly Asn Leu Thr Arg Pro Asp
            660                 665                 670

Ile Thr Phe Thr Tyr Phe Gln Pro Lys Pro Arg Gln Ala Trp Val Trp
        675                 680                 685

Ala Ala Val Arg Gly Pro Cys Ser Val Ser Cys Gly Ala Gly Leu Arg
    690                 695                 700

Trp Val Asn Tyr Ser Cys Leu Asp Gln Ala Arg Lys Glu Leu Val Glu
705                 710                 715                 720

Thr Val Gln Cys Gln Gly Ser Gln Gln Pro Pro Ala Trp Pro Glu Ala
                725                 730                 735

Cys Val Leu Glu Pro Cys Pro Pro Tyr Trp Ala Val Gly Asp Phe Gly
            740                 745                 750
```

-continued

Pro Cys Ser Ala Ser Cys Gly Gly Leu Arg Glu Arg Pro Val Arg
    755                 760                 765

Cys Val Glu Ala Gln Gly Ser Leu Leu Lys Thr Leu Pro Pro Ala Arg
770                 775                 780

Cys Arg Ala Gly Ala Gln Gln Pro Ala Val Ala Leu Glu Thr Cys Asn
785                 790                 795                 800

Pro Gln Pro Cys Pro Ala Arg Trp Glu Val Ser Pro Ser Ser Cys
                805                 810                 815

Thr Ser Ala Gly Ala Gly Leu Ala Leu Glu Asn Glu Thr Cys Val
                820                 825                 830

Pro Gly Ala Asp Gly Leu Glu Ala Pro Val Thr Glu Gly Pro Gly Ser
    835                 840                 845

Val Asp Glu Lys Leu Pro Ala Pro Glu Pro Cys Val Gly Met Ser Cys
850                 855                 860

Pro Pro Gly Trp Gly His Leu Asp Ala Thr Ser Ala Gly Glu Lys Ala
865                 870                 875                 880

Pro Ser Pro Trp Gly Ser Ile Arg Thr Gly Ala Gln Ala Ala His Val
                885                 890                 895

Trp Thr Pro Ala Ala Gly Ser Cys Ser Val Ser Cys Gly Arg Gly Leu
            900                 905                 910

Met Glu Leu Arg Phe Leu Cys Met Asp Ser Ala Leu Arg Val Pro Val
            915                 920                 925

Gln Glu Glu Leu Cys Gly Leu Ala Ser Lys Pro Gly Ser Arg Arg Glu
    930                 935                 940

Val Cys Gln Ala Val Pro Cys Pro Ala Arg Trp Gln Tyr Lys Leu Ala
945                 950                 955                 960

Ala Cys Ser Val Ser Cys Gly Arg Gly Val Val Arg Arg Ile Leu Tyr
                965                 970                 975

Cys Ala Arg Ala His Gly Glu Asp Asp Gly Glu Glu Ile Leu Leu Asp
            980                 985                 990

Thr Gln Cys Gln Gly Leu Pro Arg Pro Glu Pro Gln Glu Ala Cys Ser
            995                 1000                1005

Leu Glu Pro Cys Pro Pro Arg Trp Lys Val Met Ser Leu Gly Pro
    1010                1015                1020

Cys Ser Ala Ser Cys Gly Leu Gly Thr Ala Arg Arg Ser Val Ala
    1025                1030                1035

Cys Val Gln Leu Asp Gln Gly Gln Asp Val Glu Val Asp Glu Ala
    1040                1045                1050

Ala Cys Ala Ala Leu Val Arg Pro Glu Ala Ser Val Pro Cys Leu
    1055                1060                1065

Ile Ala Asp Cys Thr Tyr Arg Trp His Val Gly Thr Trp Met Glu
    1070                1075                1080

Cys Ser Val Ser Cys Gly Asp Gly Ile Gln Arg Arg Arg Asp Thr
    1085                1090                1095

Cys Leu Gly Pro Gln Ala Gln Ala Pro Val Pro Ala Asp Phe Cys
    1100                1105                1110

Gln His Leu Pro Lys Pro Val Thr Val Arg Gly Cys Trp Ala Gly
    1115                1120                1125

Pro Cys Val Gly Gln Gly Thr Pro Ser Leu Val Pro His Glu Glu
    1130                1135                1140

Ala Ala Ala Pro Gly Arg Thr Thr Ala Thr Pro Ala Gly Ala Ser
    1145                1150                1155

-continued

Leu Glu Trp Ser Gln Ala Arg Gly Leu Leu Phe Ser Pro Ala Pro
1160                1165                1170

Gln Pro Arg Arg Leu Leu Pro Gly Pro Gln Glu Asn Ser Val Gln
    1175                1180                1185

Ser Ser Ala Cys Gly Arg Gln His Leu Glu Pro Thr Gly Thr Ile
    1190                1195                1200

Asp Met Arg Gly Pro Gly Gln Ala Asp Cys Ala Val Ala Ile Gly
    1205                1210                1215

Arg Pro Leu Gly Glu Val Val Thr Leu Arg Val Leu Glu Ser Ser
    1220                1225                1230

Leu Asn Cys Ser Ala Gly Asp Met Leu Leu Leu Trp Gly Arg Leu
    1235                1240                1245

Thr Trp Arg Lys Met Cys Arg Lys Leu Leu Asp Met Thr Phe Ser
    1250                1255                1260

Ser Lys Thr Asn Thr Leu Val Val Arg Gln Arg Cys Gly Arg Pro
    1265                1270                1275

Gly Gly Gly Val Leu Leu Arg Tyr Gly Ser Gln Leu Ala Pro Glu
    1280                1285                1290

Thr Phe Tyr Arg Glu Cys Asp Met Gln Leu Phe Gly Pro Trp Gly
    1295                1300                1305

Glu Ile Val Ser Pro Ser Leu Ser Pro Ala Thr Ser Asn Ala Gly
    1310                1315                1320

Gly Cys Arg Leu Phe Ile Asn Val Ala Pro His Ala Arg Ile Ala
    1325                1330                1335

Ile His Ala Leu Ala Thr Asn Met Gly Ala Gly Thr Glu Gly Ala
    1340                1345                1350

Asn Ala Ser Tyr Ile Leu Ile Arg Asp Thr His Ser Leu Arg Thr
    1355                1360                1365

Thr Ala Phe His Gly Gln Gln Val Leu Tyr Trp Glu Ser Glu Ser
    1370                1375                1380

Ser Gln Ala Glu Met Glu Phe Ser Glu Gly Phe Leu Lys Ala Gln
    1385                1390                1395

Ala Ser Leu Arg Gly Gln Tyr Trp Thr Leu Gln Ser Trp Val Pro
    1400                1405                1410

Glu Met Gln Asp Pro Gln Ser Trp Lys Gly Lys Glu Gly Thr
    1415                1420                1425

<210> SEQ ID NO 4
<211> LENGTH: 1371
<212> TYPE: PRT
<213> ORGANISM: Homo sapiens
<220> FEATURE:
<223> OTHER INFORMATION: A disintegrin and metalloproteinase with
      thrombospondin motifs 13 (Human) isoform 2

<400> SEQUENCE: 4

Met His Gln Arg His Pro Arg Ala Arg Cys Pro Pro Leu Cys Val Ala
1               5                   10                  15

Gly Ile Leu Ala Cys Gly Phe Leu Leu Gly Cys Trp Gly Pro Ser His
                20                  25                  30

Phe Gln Gln Ser Cys Leu Gln Ala Leu Glu Pro Gln Ala Val Ser Ser
            35                  40                  45

Tyr Leu Ser Pro Gly Ala Pro Leu Lys Gly Arg Pro Pro Ser Pro Gly
        50                  55                  60

Phe Gln Arg Gln Arg Gln Arg Gln Arg Arg Ala Ala Gly Gly Ile Leu
65                  70                  75                  80

-continued

His Leu Glu Leu Leu Val Ala Val Gly Pro Asp Val Phe Gln Ala His
                 85                  90                  95

Gln Glu Asp Thr Glu Arg Tyr Val Leu Thr Asn Leu Asn Ile Gly Ala
            100                 105                 110

Glu Leu Leu Arg Asp Pro Ser Leu Gly Ala Gln Phe Arg Val His Leu
            115                 120                 125

Val Lys Met Val Ile Leu Thr Glu Pro Glu Gly Ala Pro Asn Ile Thr
130                 135                 140

Ala Asn Leu Thr Ser Ser Leu Leu Ser Val Cys Gly Trp Ser Gln Thr
145                 150                 155                 160

Ile Asn Pro Glu Asp Asp Thr Asp Pro Gly His Ala Asp Leu Val Leu
                165                 170                 175

Tyr Ile Thr Arg Phe Asp Leu Glu Leu Pro Asp Gly Asn Arg Gln Val
                180                 185                 190

Arg Gly Val Thr Gln Leu Gly Gly Ala Cys Ser Pro Thr Trp Ser Cys
            195                 200                 205

Leu Ile Thr Glu Asp Thr Gly Phe Asp Leu Gly Val Thr Ile Ala His
            210                 215                 220

Glu Ile Gly His Ser Phe Gly Leu Glu His Asp Gly Ala Pro Gly Ser
225                 230                 235                 240

Gly Cys Gly Pro Ser Gly His Val Met Ala Ser Asp Gly Ala Ala Pro
                245                 250                 255

Arg Ala Gly Leu Ala Trp Ser Pro Cys Ser Arg Arg Gln Leu Leu Ser
                260                 265                 270

Leu Leu Ser Ala Gly Arg Ala Arg Cys Val Trp Asp Pro Pro Arg Pro
            275                 280                 285

Gln Pro Gly Ser Ala Gly His Pro Pro Asp Ala Gln Pro Gly Leu Tyr
            290                 295                 300

Tyr Ser Ala Asn Glu Gln Cys Arg Val Ala Phe Gly Pro Lys Ala Val
305                 310                 315                 320

Ala Cys Thr Phe Ala Arg Glu His Leu Asp Met Cys Gln Ala Leu Ser
                325                 330                 335

Cys His Thr Asp Pro Leu Asp Gln Ser Ser Cys Ser Arg Leu Leu Val
                340                 345                 350

Pro Leu Leu Asp Gly Thr Glu Cys Gly Val Glu Lys Trp Cys Ser Lys
            355                 360                 365

Gly Arg Cys Arg Ser Leu Val Glu Leu Thr Pro Ile Ala Ala Val His
            370                 375                 380

Gly Arg Trp Ser Ser Trp Gly Pro Arg Ser Pro Cys Ser Arg Ser Cys
385                 390                 395                 400

Gly Gly Gly Val Val Thr Arg Arg Gln Cys Asn Asn Pro Arg Pro
                405                 410                 415

Ala Phe Gly Gly Arg Ala Cys Val Gly Ala Asp Leu Gln Ala Glu Met
                420                 425                 430

Cys Asn Thr Gln Ala Cys Glu Lys Thr Gln Leu Glu Phe Met Ser Gln
            435                 440                 445

Gln Cys Ala Arg Thr Asp Gly Gln Pro Leu Arg Ser Ser Pro Gly Gly
            450                 455                 460

Ala Ser Phe Tyr His Trp Gly Ala Ala Val Pro His Ser Gln Gly Asp
465                 470                 475                 480

Ala Leu Cys Arg His Met Cys Arg Ala Ile Gly Glu Ser Phe Ile Met
                485                 490                 495

-continued

```
Lys Arg Gly Asp Ser Phe Leu Asp Gly Thr Arg Cys Met Pro Ser Gly
                500                 505                 510

Pro Arg Glu Asp Gly Thr Leu Ser Leu Cys Val Ser Gly Ser Cys Arg
            515                 520                 525

Thr Phe Gly Cys Asp Gly Arg Met Asp Ser Gln Gln Val Trp Asp Arg
        530                 535                 540

Cys Gln Val Cys Gly Gly Asp Asn Ser Thr Cys Ser Pro Arg Lys Gly
545                 550                 555                 560

Ser Phe Thr Ala Gly Arg Ala Arg Glu Tyr Val Thr Phe Leu Thr Val
                565                 570                 575

Thr Pro Asn Leu Thr Ser Val Tyr Ile Ala Asn His Arg Pro Leu Phe
            580                 585                 590

Thr His Leu Ala Val Arg Ile Gly Gly Arg Tyr Val Val Ala Gly Lys
        595                 600                 605

Met Ser Ile Ser Pro Asn Thr Thr Tyr Pro Ser Leu Leu Glu Asp Gly
610                 615                 620

Arg Val Glu Tyr Arg Val Ala Leu Thr Glu Asp Arg Leu Pro Arg Leu
625                 630                 635                 640

Glu Glu Ile Arg Ile Trp Gly Pro Leu Gln Glu Asp Ala Asp Ile Gln
                645                 650                 655

Val Tyr Arg Arg Tyr Gly Glu Glu Tyr Gly Asn Leu Thr Arg Pro Asp
            660                 665                 670

Ile Thr Phe Thr Tyr Phe Gln Pro Lys Pro Arg Gln Ala Trp Val Trp
        675                 680                 685

Ala Ala Val Arg Gly Pro Cys Ser Val Ser Cys Gly Ala Gly Leu Arg
        690                 695                 700

Trp Val Asn Tyr Ser Cys Leu Asp Gln Ala Arg Lys Glu Leu Val Glu
705                 710                 715                 720

Thr Val Gln Cys Gln Gly Ser Gln Gln Pro Ala Trp Pro Glu Ala
                725                 730                 735

Cys Val Leu Glu Pro Cys Pro Pro Tyr Trp Ala Val Gly Asp Phe Gly
            740                 745                 750

Pro Cys Ser Ala Ser Cys Gly Gly Gly Leu Arg Glu Arg Pro Val Arg
        755                 760                 765

Cys Val Glu Ala Gln Gly Ser Leu Leu Lys Thr Leu Pro Pro Ala Arg
        770                 775                 780

Cys Arg Ala Gly Ala Gln Gln Pro Ala Val Ala Leu Glu Thr Cys Asn
785                 790                 795                 800

Pro Gln Pro Cys Pro Ala Arg Trp Glu Val Ser Glu Pro Ser Ser Cys
                805                 810                 815

Thr Ser Ala Gly Gly Ala Gly Leu Ala Leu Glu Asn Glu Thr Cys Val
            820                 825                 830

Pro Gly Ala Asp Gly Leu Glu Ala Pro Val Thr Glu Gly Pro Gly Ser
        835                 840                 845

Val Asp Glu Lys Leu Pro Ala Pro Glu Pro Cys Val Gly Met Ser Cys
850                 855                 860

Pro Pro Gly Trp Gly His Leu Asp Ala Thr Ser Ala Gly Glu Lys Ala
865                 870                 875                 880

Pro Ser Pro Trp Gly Ser Ile Arg Thr Gly Ala Gln Ala Ala His Val
                885                 890                 895

Trp Thr Pro Ala Ala Gly Ser Cys Ser Val Ser Cys Gly Arg Gly Leu
            900                 905                 910
```

-continued

Met Glu Leu Arg Phe Leu Cys Met Asp Ser Ala Leu Arg Val Pro Val
    915                 920                 925

Gln Glu Glu Leu Cys Gly Leu Ala Ser Lys Pro Gly Ser Arg Arg Glu
    930                 935                 940

Val Cys Gln Ala Val Pro Cys Pro Ala Arg Trp Gln Tyr Lys Leu Ala
945                 950                 955                 960

Ala Cys Ser Val Ser Cys Gly Arg Gly Val Val Arg Ile Leu Tyr
                965                 970                 975

Cys Ala Arg Ala His Gly Glu Asp Asp Gly Glu Glu Ile Leu Leu Asp
                980                 985                 990

Thr Gln Cys Gln Gly Leu Pro Arg Pro Glu Pro Gln Glu Ala Cys Ser
                995                 1000                1005

Leu Glu Pro Cys Pro Pro Arg Trp Lys Val Met Ser Leu Gly Pro
    1010                1015                1020

Cys Ser Ala Ser Cys Gly Leu Gly Thr Ala Arg Arg Ser Val Ala
    1025                1030                1035

Cys Val Gln Leu Asp Gln Gly Gln Asp Val Glu Val Asp Glu Ala
    1040                1045                1050

Ala Cys Ala Ala Leu Val Arg Pro Glu Ala Ser Val Pro Cys Leu
    1055                1060                1065

Ile Ala Asp Cys Thr Tyr Arg Trp His Val Gly Thr Trp Met Glu
    1070                1075                1080

Cys Ser Val Ser Cys Gly Asp Gly Ile Gln Arg Arg Arg Asp Thr
    1085                1090                1095

Cys Leu Gly Pro Gln Ala Gln Ala Pro Val Pro Ala Asp Phe Cys
    1100                1105                1110

Gln His Leu Pro Lys Pro Val Thr Val Arg Gly Cys Trp Ala Gly
    1115                1120                1125

Pro Cys Val Gly Gln Gly Ala Cys Gly Arg Gln His Leu Glu Pro
    1130                1135                1140

Thr Gly Thr Ile Asp Met Arg Gly Pro Gly Gln Ala Asp Cys Ala
    1145                1150                1155

Val Ala Ile Gly Arg Pro Leu Gly Glu Val Val Thr Leu Arg Val
    1160                1165                1170

Leu Glu Ser Ser Leu Asn Cys Ser Ala Gly Asp Met Leu Leu Leu
    1175                1180                1185

Trp Gly Arg Leu Thr Trp Arg Lys Met Cys Arg Lys Leu Leu Asp
    1190                1195                1200

Met Thr Phe Ser Ser Lys Thr Asn Thr Leu Val Val Arg Gln Arg
    1205                1210                1215

Cys Gly Arg Pro Gly Gly Gly Val Leu Leu Arg Tyr Gly Ser Gln
    1220                1225                1230

Leu Ala Pro Glu Thr Phe Tyr Arg Glu Cys Asp Met Gln Leu Phe
    1235                1240                1245

Gly Pro Trp Gly Glu Ile Val Ser Pro Ser Leu Ser Pro Ala Thr
    1250                1255                1260

Ser Asn Ala Gly Gly Cys Arg Leu Phe Ile Asn Val Ala Pro His
    1265                1270                1275

Ala Arg Ile Ala Ile His Ala Leu Ala Thr Asn Met Gly Ala Gly
    1280                1285                1290

Thr Glu Gly Ala Asn Ala Ser Tyr Ile Leu Ile Arg Asp Thr His
    1295                1300                1305

-continued

```
Ser Leu Arg Thr Thr Ala Phe His Gly Gln Gln Val Leu Tyr Trp
    1310                1315                1320

Glu Ser Glu Ser Ser Gln Ala Glu Met Glu Phe Ser Glu Gly Phe
1325                1330                1335

Leu Lys Ala Gln Ala Ser Leu Arg Gly Gln Tyr Trp Thr Leu Gln
    1340                1345                1350

Ser Trp Val Pro Glu Met Gln Asp Pro Gln Ser Trp Lys Gly Lys
    1355                1360                1365

Glu Gly Thr
    1370

<210> SEQ ID NO 5
<211> LENGTH: 1340
<212> TYPE: PRT
<213> ORGANISM: Homo sapiens
<220> FEATURE:
<223> OTHER INFORMATION: A disintegrin and metalloproteinase with
      thrombospondin motifs 13 (Human) isoform 3

<400> SEQUENCE: 5

Met His Gln Arg His Pro Arg Ala Arg Cys Pro Pro Leu Cys Val Ala
1               5                   10                  15

Gly Ile Leu Ala Cys Gly Phe Leu Leu Gly Cys Trp Gly Pro Ser His
            20                  25                  30

Phe Gln Gln Ser Cys Leu Gln Ala Leu Glu Pro Gln Ala Val Ser Ser
        35                  40                      45

Tyr Leu Ser Pro Gly Ala Pro Leu Lys Gly Arg Pro Pro Ser Pro Gly
    50                  55                      60

Phe Gln Arg Gln Arg Gln Arg Gln Arg Arg Ala Ala Gly Gly Ile Leu
65                  70                  75                  80

His Leu Glu Leu Leu Val Ala Val Gly Pro Asp Val Phe Gln Ala His
                85                  90                  95

Gln Glu Asp Thr Glu Arg Tyr Val Leu Thr Asn Leu Asn Ile Gly Ala
            100                 105                 110

Glu Leu Leu Arg Asp Pro Ser Leu Gly Ala Gln Phe Arg Val His Leu
        115                 120                 125

Val Lys Met Val Ile Leu Thr Glu Pro Glu Gly Ala Pro Asn Ile Thr
    130                 135                 140

Ala Asn Leu Thr Ser Ser Leu Leu Ser Val Cys Gly Trp Ser Gln Thr
145                 150                 155                 160

Ile Asn Pro Glu Asp Asp Thr Asp Pro Gly His Ala Asp Leu Val Leu
                165                 170                 175

Tyr Ile Thr Arg Phe Asp Leu Glu Leu Pro Asp Gly Asn Arg Gln Val
            180                 185                 190

Arg Gly Val Thr Gln Leu Gly Gly Ala Cys Ser Pro Thr Trp Ser Cys
        195                 200                 205

Leu Ile Thr Glu Asp Thr Gly Phe Asp Leu Gly Val Thr Ile Ala His
    210                 215                 220

Glu Ile Gly His Ser Phe Gly Leu Glu His Asp Gly Ala Pro Gly Ser
225                 230                 235                 240

Gly Cys Gly Pro Ser Gly His Val Met Ala Ser Asp Gly Ala Ala Pro
                245                 250                 255

Arg Ala Gly Leu Ala Trp Ser Pro Cys Ser Arg Arg Gln Leu Leu Ser
            260                 265                 270

Leu Leu Ser Ala Asn Glu Gln Cys Arg Val Ala Phe Gly Pro Lys Ala
        275                 280                 285
```

```
Val Ala Cys Thr Phe Ala Arg Glu His Leu Asp Met Cys Gln Ala Leu
    290                 295                 300
Ser Cys His Thr Asp Pro Leu Asp Gln Ser Ser Cys Ser Arg Leu Leu
305                 310                 315                 320
Val Pro Leu Leu Asp Gly Thr Glu Cys Gly Val Glu Lys Trp Cys Ser
                325                 330                 335
Lys Gly Arg Cys Arg Ser Leu Val Glu Leu Thr Pro Ile Ala Ala Val
                340                 345                 350
His Gly Arg Trp Ser Ser Trp Gly Pro Arg Ser Pro Cys Ser Arg Ser
                355                 360                 365
Cys Gly Gly Val Val Thr Arg Arg Gln Cys Asn Asn Pro Arg
    370                 375                 380
Pro Ala Phe Gly Gly Arg Ala Cys Val Gly Ala Asp Leu Gln Ala Glu
385                 390                 395                 400
Met Cys Asn Thr Gln Ala Cys Glu Lys Thr Gln Leu Glu Phe Met Ser
                405                 410                 415
Gln Gln Cys Ala Arg Thr Asp Gly Gln Pro Leu Arg Ser Ser Pro Gly
                420                 425                 430
Gly Ala Ser Phe Tyr His Trp Gly Ala Ala Val Pro His Ser Gln Gly
                435                 440                 445
Asp Ala Leu Cys Arg His Met Cys Arg Ala Ile Gly Glu Ser Phe Ile
                450                 455                 460
Met Lys Arg Gly Asp Ser Phe Leu Asp Gly Thr Arg Cys Met Pro Ser
465                 470                 475                 480
Gly Pro Arg Glu Asp Gly Thr Leu Ser Leu Cys Val Ser Gly Ser Cys
                485                 490                 495
Arg Thr Phe Gly Cys Asp Gly Arg Met Asp Ser Gln Val Trp Asp
                500                 505                 510
Arg Cys Gln Val Cys Gly Gly Asp Asn Ser Thr Cys Ser Pro Arg Lys
                515                 520                 525
Gly Ser Phe Thr Ala Gly Arg Ala Arg Glu Tyr Val Thr Phe Leu Thr
530                 535                 540
Val Thr Pro Asn Leu Thr Ser Val Tyr Ile Ala Asn His Arg Pro Leu
545                 550                 555                 560
Phe Thr His Leu Ala Val Arg Ile Gly Gly Arg Tyr Val Val Ala Gly
                565                 570                 575
Lys Met Ser Ile Ser Pro Asn Thr Thr Tyr Pro Ser Leu Leu Glu Asp
                580                 585                 590
Gly Arg Val Glu Tyr Arg Val Ala Leu Thr Glu Asp Arg Leu Pro Arg
                595                 600                 605
Leu Glu Glu Ile Arg Ile Trp Gly Pro Leu Gln Glu Asp Ala Asp Ile
                610                 615                 620
Gln Val Tyr Arg Arg Tyr Gly Glu Glu Tyr Gly Asn Leu Thr Arg Pro
625                 630                 635                 640
Asp Ile Thr Phe Thr Tyr Phe Gln Pro Lys Pro Arg Gln Ala Trp Val
                645                 650                 655
Trp Ala Ala Val Arg Gly Pro Cys Ser Val Ser Cys Gly Ala Gly Leu
                660                 665                 670
Arg Trp Val Asn Tyr Ser Cys Leu Asp Gln Ala Arg Lys Glu Leu Val
                675                 680                 685
Glu Thr Val Gln Cys Gln Gly Ser Gln Gln Pro Pro Ala Trp Pro Glu
690                 695                 700
```

```
Ala Cys Val Leu Glu Pro Cys Pro Pro Tyr Trp Ala Val Gly Asp Phe
705                 710                 715                 720

Gly Pro Cys Ser Ala Ser Cys Gly Gly Gly Leu Arg Glu Arg Pro Val
            725                 730                 735

Arg Cys Val Glu Ala Gln Gly Ser Leu Leu Lys Thr Leu Pro Pro Ala
            740                 745                 750

Arg Cys Arg Ala Gly Ala Gln Gln Pro Ala Val Ala Leu Glu Thr Cys
            755                 760                 765

Asn Pro Gln Pro Cys Pro Ala Arg Trp Glu Val Ser Glu Pro Ser Ser
            770                 775                 780

Cys Thr Ser Ala Gly Gly Ala Gly Leu Ala Leu Glu Asn Glu Thr Cys
785                 790                 795                 800

Val Pro Gly Ala Asp Gly Leu Glu Ala Pro Val Thr Glu Gly Pro Gly
            805                 810                 815

Ser Val Asp Glu Lys Leu Pro Ala Pro Glu Pro Cys Val Gly Met Ser
            820                 825                 830

Cys Pro Pro Gly Trp Gly His Leu Asp Ala Thr Ser Ala Gly Glu Lys
            835                 840                 845

Ala Pro Ser Pro Trp Gly Ser Ile Arg Thr Gly Ala Gln Ala Ala His
850                 855                 860

Val Trp Thr Pro Ala Ala Gly Ser Cys Ser Val Ser Cys Gly Arg Gly
865                 870                 875                 880

Leu Met Glu Leu Arg Phe Leu Cys Met Asp Ser Ala Leu Arg Val Pro
            885                 890                 895

Val Gln Glu Glu Leu Cys Gly Leu Ala Ser Lys Pro Gly Ser Arg Arg
            900                 905                 910

Glu Val Cys Gln Ala Val Pro Cys Pro Ala Arg Trp Gln Tyr Lys Leu
            915                 920                 925

Ala Ala Cys Ser Val Ser Cys Gly Arg Gly Val Val Arg Arg Ile Leu
            930                 935                 940

Tyr Cys Ala Arg Ala His Gly Glu Asp Asp Gly Glu Glu Ile Leu Leu
945                 950                 955                 960

Asp Thr Gln Cys Gln Gly Leu Pro Arg Pro Glu Pro Gln Glu Ala Cys
            965                 970                 975

Ser Leu Glu Pro Cys Pro Pro Arg Trp Lys Val Met Ser Leu Gly Pro
            980                 985                 990

Cys Ser Ala Ser Cys Gly Leu Gly Thr Ala Arg Arg Ser Val Ala Cys
            995                 1000                1005

Val Gln Leu Asp Gln Gly Gln Asp Val Glu Val Asp Glu Ala Ala
            1010                1015                1020

Cys Ala Ala Leu Val Arg Pro Glu Ala Ser Val Pro Cys Leu Ile
            1025                1030                1035

Ala Asp Cys Thr Tyr Arg Trp His Val Gly Thr Trp Met Glu Cys
            1040                1045                1050

Ser Val Ser Cys Gly Asp Gly Ile Gln Arg Arg Arg Asp Thr Cys
            1055                1060                1065

Leu Gly Pro Gln Ala Gln Ala Pro Val Pro Ala Asp Phe Cys Gln
            1070                1075                1080

His Leu Pro Lys Pro Val Thr Val Arg Gly Cys Trp Ala Gly Pro
            1085                1090                1095

Cys Val Gly Gln Gly Ala Cys Gly Arg Gln His Leu Glu Pro Thr
            1100                1105                1110
```

-continued

```
Gly Thr Ile Asp Met Arg Gly Pro Gly Gln Ala Asp Cys Ala Val
    1115                1120                1125

Ala Ile Gly Arg Pro Leu Gly Glu Val Val Thr Leu Arg Val Leu
    1130                1135                1140

Glu Ser Ser Leu Asn Cys Ser Ala Gly Asp Met Leu Leu Leu Trp
    1145                1150                1155

Gly Arg Leu Thr Trp Arg Lys Met Cys Arg Lys Leu Leu Asp Met
    1160                1165                1170

Thr Phe Ser Ser Lys Thr Asn Thr Leu Val Val Arg Gln Arg Cys
    1175                1180                1185

Gly Arg Pro Gly Gly Val Leu Leu Arg Tyr Gly Ser Gln Leu
    1190                1195                1200

Ala Pro Glu Thr Phe Tyr Arg Glu Cys Asp Met Gln Leu Phe Gly
    1205                1210                1215

Pro Trp Gly Glu Ile Val Ser Pro Ser Leu Ser Pro Ala Thr Ser
    1220                1225                1230

Asn Ala Gly Gly Cys Arg Leu Phe Ile Asn Val Ala Pro His Ala
    1235                1240                1245

Arg Ile Ala Ile His Ala Leu Ala Thr Asn Met Gly Ala Gly Thr
    1250                1255                1260

Glu Gly Ala Asn Ala Ser Tyr Ile Leu Ile Arg Asp Thr His Ser
    1265                1270                1275

Leu Arg Thr Thr Ala Phe His Gly Gln Gln Val Leu Tyr Trp Glu
    1280                1285                1290

Ser Glu Ser Ser Gln Ala Glu Met Glu Phe Ser Glu Gly Phe Leu
    1295                1300                1305

Lys Ala Gln Ala Ser Leu Arg Gly Gln Tyr Trp Thr Leu Gln Ser
    1310                1315                1320

Trp Val Pro Glu Met Gln Asp Pro Gln Ser Trp Lys Gly Lys Glu
    1325                1330                1335

Gly Thr
    1340
```

<210> SEQ ID NO 6
<211> LENGTH: 73
<212> TYPE: PRT
<213> ORGANISM: Artificial Sequence
<220> FEATURE:
<223> OTHER INFORMATION: Description of Artificial Sequence: Synthetic
      polymer polypeptide

<400> SEQUENCE: 6

```
Asp Arg Glu Gln Ala Pro Asn Leu Val Tyr Met Val Thr Gly Asn Pro
1               5                   10                  15

Ala Ser Asp Glu Ile Lys Arg Leu Pro Gly Asp Ile Gln Val Val Pro
            20                  25                  30

Ile Gly Val Gly Pro Asn Ala Asn Val Gln Glu Leu Glu Arg Ile Gly
        35                  40                  45

Trp Pro Asn Ala Pro Ile Leu Ile Gln Asp Phe Glu Thr Leu Pro Arg
    50                  55                  60

Glu Ala Pro Asp Leu Val Leu Gln Arg
65                  70
```

<210> SEQ ID NO 7
<211> LENGTH: 55
<212> TYPE: PRT
<213> ORGANISM: Artificial Sequence

```
<220> FEATURE:
<223> OTHER INFORMATION: Description of Artificial Sequence: Synthetic
      polymer polypeptide

<400> SEQUENCE: 7

Asp Arg Glu Lys Ala Pro Asn Leu Val Tyr Met Val Thr Gly Cys Pro
1               5                   10                  15

Ala Ser Asp Glu Ile Lys Arg Leu Pro Gly Asp Ile Ile Gly Trp Pro
                20                  25                  30

Asn Ala Pro Ile Leu Ile Gln Asp Phe Glu Thr Leu Pro Arg Glu Ala
            35                  40                  45

Pro Asp Leu Val Leu Gln Arg
    50                  55

<210> SEQ ID NO 8
<211> LENGTH: 171
<212> TYPE: PRT
<213> ORGANISM: Homo sapiens

<400> SEQUENCE: 8

Asp Val Ala Phe Val Leu Glu Gly Ser Asp Lys Ile Gly Glu Ala Asp
1               5                   10                  15

Phe Asn Arg Ser Lys Glu Phe Met Glu Glu Val Ile Gln Arg Met Asp
                20                  25                  30

Val Gly Gln Asp Ser Ile His Val Thr Val Leu Gln Tyr Ser Tyr Met
                35                  40                  45

Val Thr Val Glu Tyr Pro Phe Ser Glu Ala Gln Ser Lys Gly Asp Ile
    50                  55                  60

Leu Gln Arg Val Arg Glu Ile Arg Tyr Gln Gly Gly Asn Arg Thr Asn
65                  70                  75                  80

Thr Gly Leu Ala Leu Arg Tyr Leu Ser Asp His Ser Phe Leu Val Ser
                85                  90                  95

Gln Gly Asp Arg Glu Gln Ala Pro Asn Leu Val Tyr Met Val Thr Gly
                100                 105                 110

Asn Pro Ala Ser Asp Glu Ile Lys Arg Leu Pro Gly Asp Ile Gln Val
            115                 120                 125

Val Pro Ile Gly Val Gly Pro Asn Ala Asn Val Gln Glu Leu Glu Arg
    130                 135                 140

Ile Gly Trp Pro Asn Ala Pro Ile Leu Ile Gln Asp Phe Glu Thr Leu
145                 150                 155                 160

Pro Arg Glu Ala Pro Asp Leu Val Leu Gln Arg
                165                 170
```

POLYPEPTIDE SUBSTRATE FOR THE DETECTION OF VON WILLIEBRAND FACTOR CLEAVING PROTEASE ADAMTS13

CROSS REFERENCE TO RELATED APPLICATIONS

This application is a continuation of U.S. patent application Ser. No. 14/357,988, filed May 13, 2014, which is a National Stage application of PCT International Application No. PCT/US2012/064526, filed Nov. 9, 2012, which claims the benefit of priority to U.S. Provisional Application No. 61/558,927, filed on Nov. 11, 2011, the entire contents of which are hereby incorporated by reference.

BACKGROUND von Willebrand factor (VWF) is a large multimeric plasma glycoprotein crucial in the maintenance of hemostasis by functioning as both an antihemophilic factor carrier and a platelet-vessel wall mediator in the blood coagulation system, mainly by mediating tethering and adhesion of circulating platelets at sites of vascular injury. Mutations in this gene or deficiencies in this protein result in von Willebrand's disease (VWD).

VWF is expressed by endothelial cells and megakaryocytes. It is synthesized as 250-kDa monomers, which undergo intracellular processing, glycosylation, multimerization and propeptide removal that leads to formation of mature VWF multimers.

VWF multimeric size is modulated by the plasma metallopeptidase ADAMTS13 (a disintegrin and metallopeptidase with thrombospondin type 1 motif, member 13, a "cleaving protease"), which cleaves at a single site in the VWF A2 domain (AA1498-1665; UniProtKB/Swiss-Pro database; Accession: P04275. SEQ ID NO: 2) between Y1605 and M1606.

ADAMTS13 is a protease that is activated in the presence of barium and other metal ions. ADAMTS13 has been demonstrated to degrade full-length multimeric vWF into multimers of smaller size and into lower molecular weight polypeptides or peptides. For this reason, the ADAMTS13 protease has been termed vWF-cleaving protease or the "ATS protease". The activity of the protease has been demonstrated to be reduced in patients with Thrombotic Thrombocytopenia Purpura (TTP).

Severe deficiency of the protease has been described in patients with chronic relapsing TTP, a deficiency that may be inherited or acquired as a result of an autoimmune mechanism.

In the past, assays for the presence or absence of ADAMTS13 utilized a cumbersome technique in which plasma from a patient is incubated with exogenous multimeric vWF in the presence of barium chloride on the surface of a membrane floating on a buffer containing 1.5 molar urea. More recently an alternative method has been developed by Kokame et al. (Kokame, K., Y. Nobe, Y. Kokubo, A. Okayama, and T. Miyata. 2005. FRETS-VWF73, a first fluorogenic substrate for ADAMTS13 assay. *Br. J. Haematol.* 129:93-100. See also Wu J J, Fujikawa K, McMullen B A, Chung D W. Characterization of a core binding site for ADAMTS13 in the A2 domain of von Willebrand factor. *Proc Natl Acad Sci USA*. 2006; 103: 18470-4.). Kokame's method utilizes a polypeptide substrate for ADAMTS13 activity, wherein the substrate is 73 amino acid residues in the A2 domain of VWF, called VWF73. FRETS-VWF73 is within this domain and the 73-amino-acid polypeptide sequence corresponds to the region from D1596 to R1668 of VWF (see SEQ ID NO: 6 herein), Q1599 and N1610 when substituted with A2pr(Nma) and A2pr(Dnp) respectively. Several assays have been developed using SEQ ID NO: 6. VWF73-based ADAMTS13 assays have the potential to contribute to improved clinical treatments.

However, the de novo synthesis of SEQ ID NO: 6 is difficult and the FRETS-VWF73 substrate works near the UV spectrum. The signal that is generated therefore suffers from heavy contribution of autofluorescence which can be exacerbated by the fact that the assay is homogeneous, i.e. is performed in a single step without washing away the plasma, one of the major contributors to the autofluorescence noise. Because of its susceptibility to autofluorescence, an assay based on the FRETS-VWF73 substrate is very sensitive to dust microparticles, potentially resulting in poor replicates and aberrant results. Furthermore, FRETS-VWF73 substrate assays typically result in a non-linear calibration curve which can result in low accuracy below 10% of ADAMTS13 activity. This is problematic since the resolution of ADAMTS13 activity at between 0-10% is important to clinicians to confirm the diagnosis of TTP and to monitor and fine tune the therapeutic intervention (such as plasma exchange). Further, ADAMTS13 activity assays using a SEQ ID NO: 6 polypeptide suffer from poor sensitivity.

As a result, there is a need in the art for an improved ADAMTS13 polypeptide substrate. The present invention seeks to address this need.

SUMMARY

In a first aspect, there is provided an isolated polypeptide substrate for a disintegrin-like and metallopeptidase with thrombospondin type-1 motif, 13 (ADAMTS13) that is from 45 to 70 amino acids in length and has an amino acid sequence that is substantially similar to part of the von Willebrand factor A2 domain sequence set forth in SEQ ID NO: 2, with one or more of the following modifications: (i) the amino acid corresponding to position 1599 of SEQ ID NO: 2 is mutated from Q to K; (ii) the amino acid corresponding to position 1610 of SEQ ID NO: 2 is mutated from N to C; and (iii) the amino acids corresponding to Q1624 to R1641 of SEQ ID NO: 2 are deleted.

In a second aspect, there is provided an ADAMTS13 polypeptide substrate that is from 50 to 75 amino acids in length and has an amino acid sequence that is substantially similar to part of the von Willebrand factor A2 domain sequence set forth in SEQ ID NO: 2, with one or more of the following modifications: (i) the amino acid corresponding to position 1599 of SEQ ID NO: 2 is mutated from Q to K; (ii) the amino acid corresponding to position 1610 of SEQ ID NO: 2 is mutated from N to C; (iii) the amino acid corresponding to position 1629 of SEQ ID NO: 2 is mutated from G to E; and (iv) the amino acids corresponding to G1631 to R1641 of SEQ ID NO: 2 are deleted.

Suitably, the amino acid at the N-terminus of said polypeptide substrate corresponds to D1596 of SEQ ID NO: 2.

Suitably, the amino acid at the C-terminus of said polypeptide substrate corresponds to R1668 of SEQ ID NO: 2.

Suitably, the polypeptide is a synthetic polypeptide that comprises a detectable label.

Suitably, the detectable label is a fluorophore and a quencher.

Suitably, the attachment site for the fluorophore is at the amino acid corresponding to position 1610 of SEQ ID NO: 2 and/or wherein the attachment site for the quencher is at the amino acid corresponding to position 1599 of SEQ ID NO: 2 or wherein attachment site for the quencher is at the amino acid corresponding to position 1610 of SEQ ID NO: 2 and/or wherein the attachment site for the fluorophore is at the amino acid corresponding to position 1599 of SEQ ID NO: 2.

Suitably, the ADAMTS13 polypeptide substrate comprises, consists or consists essentially of the sequence set forth in SEQ ID NO: 7.

Suitably, the ADAMTS13 polypeptide substrate comprises, consists or consists essentially of the sequence set forth in SEQ ID NO: 1.

Suitably, the ADAMTS13 polypeptide substrate is lyophilized.

In a further aspect, there is provided a method for cleaving the ADAMTS13 polypeptide substrate, comprising contacting said ADAMTS13 polypeptide substrate with an ADAMTS13 protease.

In a further aspect, there is provided a method for measuring ADAMTS13 activity in a sample comprising the use of the ADAMTS13 polypeptide substrate.

Suitably, the method comprises the steps of: (a) providing a sample comprising, or suspected of comprising, an ADAMTS13; (b) contacting said sample with the ADAMTS13 polypeptide substrate; and (c) determining the fragmentation of the ADAMTS13 polypeptide substrate, wherein the fragmentation of the ADAMTS13 polypeptide substrate is optionally compared to one or more controls and/or calibrators in order to arrive at a measurement of ADAMTS13 activity.

Suitably, the cleavage of the ADAMTS13 polypeptide substrate is measured by monitoring the change in fluorescence.

Suitably, the sample at step (a) is a plasma sample or is derived from a plasma sample.

Suitably, the ADAMTS13 polypeptide substrate is in solution during contacting step (b). Suitably, the ADAMTS13 polypeptide substrate is in solution when cleaved by a protease. Suitably, the ADAMTS13 polypeptide substrate is in solution when cleaved by an ADAMTS13 protease.

Suitably, the ADAMTS13 polypeptide substrate is attached to a solid support during contacting step (b). Suitably, the ADAMTS13 polypeptide substrate is attached to a solid support when cleaved by a protease. Suitably, the ADAMTS13 polypeptide substrate is attached to a solid support when cleaved by an ADAMTS13 protease. Suitably, the ADAMTS13 polypeptide substrate is attached to a well during contacting step (b). Suitably, the ADAMTS13 polypeptide substrate is attached to two or more wells of a microwell strip during contacting step (b). Suitably, the ADAMTS13 polypeptide substrate is attached to a bead during contacting step (b).

Suitably, step (d) is a quantitative determination of the fragmentation of the ADAMTS13 polypeptide substrate.

In a further aspect, there is provided a kit for in vitro testing of ADAMTS13 activity in a subject, comprising the ADAMTS13 polypeptide substrate, one or more calibrators containing a known concentration of ADAMTS13 activity and/or one or more positive controls for ADAMTS13 activity optionally together with a specimen diluent and/or a substrate buffer.

In a further aspect, there is provided the use of the ADAMTS13 polypeptide substrate for measuring the activity of ADAMTS13 protease in a sample.

The ADAMTS13 polypeptide substrates that are described herein have a number of advantages.

By way of example, the polypeptide substrate can be reliably synthesised. When the polypeptide substrate is synthesized by chemical synthesis it can be produced at lower cost as compared to recombinant synthesis and 73-mer synthesis.

By way of further example, a linear calibration curve can be achieved along with higher resolution, sensitivity and precision as compared to the existing ADAMTS13 activity-based assays.

By way of further example, reduced signal-to-noise ratio in the ADAMTS13 assay can be obtained.

By way of further example, faster reaction time (15 minutes or less reaction time vs. the 30 minutes required by the FRETS-VWF73-based assay) in the ADAMTS13 assay can be obtained.

By way of further example, when detectable labels are used, excitation and emission occurs at the most widely used wavelengths which makes detection simpler.

By way of further example, a higher dynamic range of the assay can be achieved resulting in the ability to precisely determine ADAMTS13 in the range of about 0-20% activity, a range that cannot be efficiently resolved in the existing activity-based assay. Thus, improvements in the differential diagnosis of TTP from other disorders including hemolytic uremic syndrome (HUS), which present similar clinical symptoms, can be achieved. Improvements in the prognostic management of TTP can also be achieved.

BRIEF DESCRIPTION OF THE DRAWINGS

FIG. 1 shows the protein sequence of a portion of VWF (AA1495-1668 of SEQ ID NO: 2) encompassing the A2 domain (AA1498-1665).

FIG. 2 shows the amino acid sequence of SEQ ID NO: 1.

DETAILED DESCRIPTION

Definitions

Figure 3:
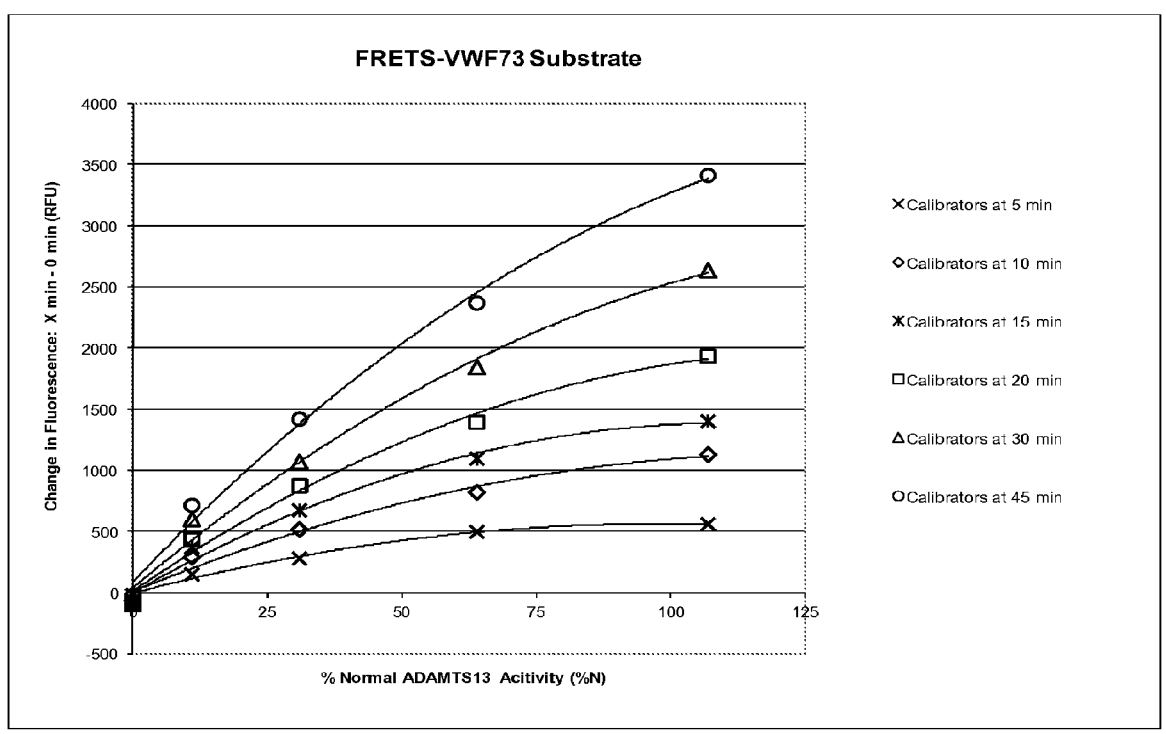
FIG. 3 displays a series of calibration curves obtained with the prior art FRETS-VWF73.

In the description that follows, a number of terms are used extensively. The following definitions are provided to facilitate understanding of the invention. The technical terms and expressions used within the scope of this application are generally to be given the meaning commonly applied to them in the art. All of the following term definitions apply to the complete content of this application. The word "comprising" does not exclude other elements or steps, and the indefinite article "a" or "an" does not exclude a plurality. The terms "essentially", "about", "approximately" and the like in the context of a given numerate value or range refers to a value or range that is within 20%, within 10%, or within 5% of the given value or range. Due to the imprecision of standard analytical methods, molecular weights and lengths of polymers are understood to be approximate values. When such a value is expressed as "about" X or "approximately" X, the stated value of X will be understood to be accurate to ±10%.

As used herein, "nucleic acid" or "nucleic acid molecule" refers to polynucleotides, such as deoxyribonucleic acid (DNA) or ribonucleic acid (RNA), oligonucleotides, amplification products, fragments generated by any of ligation, scission, endonuclease activity, and exonuclease activity, genomic DNA, recombinant vectors and chemically synthesized molecules. Nucleic acid molecules can be composed of monomers that are naturally-occurring nucleotides, or analogs of naturally-occurring nucleotides (e.g., alpha-enantiomeric forms of naturally-occurring nucleotides), or a combination of both. Nucleic acids can be either single stranded or double stranded.

The term "complement of a nucleic acid molecule" refers to a nucleic acid molecule having a complementary nucleotide sequence and reverse orientation as compared to a reference nucleotide sequence. For example, the sequence 5' ATGCACGGG 3' is complementary to 5' CCCGTGCAT 3'.

The term "degenerate nucleotide sequence" denotes a sequence of nucleotides that includes one or more degenerate codons as compared to a reference nucleic acid molecule that encodes a polypeptide. Degenerate codons contain different triplets of nucleotides, but encode the same amino acid residue (i.e., GAU and GAC triplets each encode Asp).

An "isolated nucleic acid molecule" is a nucleic acid molecule that is not integrated in the genomic nucleic acid of an organism. For example, a nucleic acid molecule that has been separated from the genomic nucleic acid of a cell is an isolated nucleic acid molecule. Another example of an isolated nucleic acid molecule is a chemically-synthesized nucleic acid molecule that is not integrated in the genome of an organism. A nucleic acid molecule that has been isolated from a particular species is smaller than the complete nucleic acid molecule of a chromosome from that species.

A "polypeptide" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptidic components, such as carbohydrate groups, fluorescent detection moieties and/or linkers. These non-peptidic components may be added to a protein by the cell in which the protein is produced, and will vary with the type of cell. Proteins are defined herein in terms of their amino acid backbone structures; non-peptidic components are generally not specified when generally referring to the amino acid sequence, but may be present nonetheless.

A peptide or polypeptide encoded by a non-host DNA molecule is a "heterologous" peptide or polypeptide.

An "isolated polypeptide" or "isolated peptide" is essentially free from contaminating cellular components, such as carbohydrate, lipid, or other proteinaceous impurities associated with the polypeptide in nature. Typically, a preparation of isolated polypeptide or isolated peptide contains the polypeptide or peptide in a highly purified form, i.e., at least 80% pure, at least 90% pure, at least 95% pure, greater than 95% pure, or greater than 99% pure. One way to show that a particular protein preparation contains an isolated polypeptide or peptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide or peptide in alternative physical forms, such as dimers or alternatively glycosylated or derivatized forms. As was described above, the term "at least 80% pure" is inclusive of all whole or partial numbers from 80% purity to 100% purity. This same applies to "at least 90% pure" and "at least 95% pure." The term "greater than 95% pure" means 95.01% to 100% purity, as described above, and including all whole and partial numbers there between.

The terms "amino-terminal" and "carboxyl-terminal" are used herein to denote positions within polypeptides or peptides. Where the context allows, these terms are used with reference to a particular sequence or portion of a polypeptide or peptide to denote proximity or relative position. For example, a certain sequence positioned carboxyl-terminal to a reference sequence within a polypeptide or peptide is located proximal to the carboxyl terminus of the reference sequence, but is not necessarily at the carboxyl terminus of the complete polypeptide or peptide.

The term "expression" refers to the biosynthesis of a gene product. For example, in the case of a structural gene, expression involves transcription of the structural gene into mRNA and the translation of mRNA into one or more polypeptides.

A "detectable label" is a molecule or atom which can be conjugated, attached to or incorporated into a polypeptide to produce a molecule useful for diagnosis. The label can be any type of label which, when attached to or incorporated into a polypeptide renders the polypeptide detectable. A detectable label may have one or more of the following characteristics: fluorescence, color, radiosensitivity, or photosensitivity. Examples of detectable labels include chelators, photoactive agents, radioisotopes, fluorescent agents, paramagnetic ions, or other marker moieties such as a fluorescent resonance energy transfer (FRET) donor and/or acceptor.

The term "affinity tag" is used herein to denote a polypeptide or peptide segment that can be attached to a second polypeptide or peptide to provide for purification or detection of the second polypeptide or peptide or provide sites for attachment of the second polypeptide or peptide to a substrate. In principal, any polypeptide or peptide for which an antibody or other specific binding agent is available can be used as an affinity tag. Affinity tags include a poly-histidine tract, protein A (Nilsson et al., EMBO J. 4:1075 (1985); Nilsson et al., Methods Enzymol. 198:3 (1991)), glutathione S transferase (Smith and Johnson, Gene 67:31 (1988)), Glu-Glu affinity tag (Grussenmeyer et al., Proc. Natl. Acad. Sci. USA 82:7952 (1985)), substance P, FLAG peptide (Hopp et al., Biotechnology 6:1204 (1988)), streptavidin binding peptide, or other antigenic epitope or binding domain. See, in general, Ford et al., Protein Expression and Purification 2:95 (1991). DNA molecules encoding affinity tags are available from commercial suppliers (e.g., Pharmacia Biotech, Piscataway, N.J.).

The term "substantially similar" when used to describe polypeptide or peptide sequences or polynucleotide sequences herein means that the two sequences share at least 70% or 75% identity over a corresponding range. More preferably, that percent identity is at least 80% identity, more preferably still at least 85%, more preferably still at least 90% identity, more preferably still at least 95% identity and most preferably at least 96%, 97%, 98% or 99% identity. Differences in identity can be due to additions, deletions or substitutions of residues in a first sequences compared to a second sequences. Those ordinarily skilled in the art will readily calculate percent identity between a polypeptide or peptide sequence or a polynucleotide sequences and a reference sequence. For example, the % identity of two polynucleotide sequences may be determined by comparing sequence information using the GAP computer program, version 6.0 described by Devereux et al. (Nucl. Acids Res.

12:387, 1984) and available from the University of Wisconsin Genetics Computer Group (UWGCG). Typical default parameters for the GAP program include: (1) a unary comparison matrix (comprising a value of 1 for identities and 0 for non-identities) for nucleotides, and the weighted comparison matrix of Gribskov and Burgess, Nucl. Acids Res. 14:6745, 1986, as described by Schwartz and Dayhoff, eds., Atlas of Protein Sequence and Structure, National Biomedical Research Foundation, pp. 353-358, 1979; (2) a penalty of 3.0 for each gap and an additional 0.10 penalty for each symbol in each gap; and (3) no penalty for end gaps. Various programs known to persons skilled in the art of sequence comparison can be alternatively utilized.

As is used herein, the terms "at least 70% identical" or "at least 70% identity" means that a polypeptide or peptide sequence or a polynucleotide sequence shares 70%-100% sequence identity with a reference sequence. This range of identity is inclusive of all whole numbers (e.g., 70%, 75%, 80%, 85%, 86%, 87%, 88%, 89%, 90%, 91%, 92%, 93%, 94%, 95%, 96%, 97%, 98%, 99% or 100%) or partial numbers (e.g., 72.15, 87.27%, 92.83%, 98.11%—to two significant figures) embraced within the recited range numbers, therefore forming a part of this description. For example, an amino acid sequence with 200 residues that share 85% identity with a reference sequence would have 170 identical residues and 30 non-identical residues. Similarly, an amino acid sequence with 235 residues may have 200 residues that are identical to a reference sequence, thus the amino acid sequence will be 85.11% identical to the reference sequence. Similarly, the terms "at least 80%," "at least 90%," "at least 95%" and "at least 99%" and the like are inclusive of all whole or partial numbers within the recited range. As is used herein, the terms "greater than 95% identical" or "greater than 95% identity" means that a sequence shares 95.01%-100% sequence identity with a reference sequence. This range is all inclusive. Differences in identity can be due to additions, deletions or substitutions of residues in a first sequences compared to a second sequence.

The term "sample" as used herein includes a biological fluid such as blood, plasma or tissue of a subject. The sample may be obtained or obtainable from a human—such as a human subject—suspected of having a disorder associated with ADAMTS13.

DETAILED DESCRIPTION OF THE INVENTION

One embodiment relates to an ADAMTS13 polypeptide substrate. Suitably, the ADAMTS13 polypeptide substrate is from 45 to 75 amino acids in length—such as from 45 to 72 amino acids in length or from 45 to 70 amino acids in length or from 50 to 75 amino acids in length. More suitably, the ADAMTS13 polypeptide substrate is from 45 to 65 amino acids in length, from 50 to 65 amino acids in length, from 50 to 60 amino acids in length, from 51 to 59 amino acids in length, from 52 to 58 amino acids in length, from 53 to 57 amino acids in length, from 54 to 56 amino acids in length, from 50 to 70 amino acids in length, from 55 to 70 amino acids in length, from 55 to 65 amino acids in length, from 60 to 65 amino acids in length, from 61 to 64 amino acids in length or from 61 to 63 amino acids in length. In one embodiment, the ADAMTS13 polypeptide substrate is from 55 to 62 amino acids in length. In one embodiment, the ADAMTS13 polypeptide substrate is 55 amino acids in length. In one embodiment, the ADAMTS13 polypeptide substrate is 62 amino acids in length. In one embodiment, the ADAMTS13 polypeptide substrate is 45, 46, 47, 48, 49, 50, 51, 52, 53, 54, 55, 56, 57, 58, 59, 60, 61, 62, 63, 64, 65, 66, 67, 68, 69, 70, 71, 72, 73, 74 or 75 amino acids in length and contains a feature as described herein.

The ADAMTS13 polypeptide substrate is an isolated chimeric or mutant amino acid construct encompassing portions of the VWF A2 domain.

In one aspect, the isolated polypeptide substrate is from 45 to 70 amino acids in length and has an amino acid sequence that is substantially similar to part of the VWF A2 domain sequence set forth in SEQ ID NO: 2, with one or more of the following modifications: (i) the amino acid corresponding to position 1599 of SEQ ID NO: 2 is mutated from Q to K; (ii) the amino acid corresponding to position 1610 of SEQ ID NO: 2 is mutated from N to C; and (iii) the amino acids corresponding to Q1624 to I1642 of SEQ ID NO: 2 are deleted.

In another aspect, the isolated polypeptide substrate is from 50 to 75 amino acids in length and has an amino acid sequence that is substantially similar to part of the VWF A2 domain sequence set forth in SEQ ID NO: 2, with one or more of the following modifications: (i) the amino acid corresponding to position 1599 of SEQ ID NO: 2 is mutated from Q to K; and (ii) the amino acid corresponding to position 1610 of SEQ ID NO: 2 is mutated from N to C; and (iii) the amino acid corresponding to position 1629 of SEQ ID NO: 2 is mutated from G to E; and (iv) the amino acids corresponding to G1631 to R1641 of SEQ ID NO: 2 are deleted.

Suitably, the amino acid at the N-terminus of said polypeptide substrate corresponds to D1596 of SEQ ID NO: 2. Suitably, the amino acid at the C-terminus of said polypeptide substrate corresponds to R1668 of SEQ ID NO: 2. Suitably, the amino acid at the N-terminus of said polypeptide substrate corresponds to D1596 of SEQ ID NO: 2 and the amino acid at the C-terminus of said polypeptide substrate corresponds to R1668 of SEQ ID NO: 2.

SEQ ID NO: 2 corresponds to a fragment of the A2 domain of VWF from *Homo Sapiens*; Accession number P04275-1 (UniProtKB/Swiss-Pro); UPI0001BBE42F (UniParc); IPI00023 014.2 (International Protein Index).

In one embodiment, the ADAMTS13 polypeptide substrate comprises, consists or consists essentially of the sequence set forth in SEQ ID NO: 7 or SEQ ID NO: 1 or a sequence that has substantial identity thereto. Isomers thereof are also contemplated. According to a further embodiment, the ADAMTS13 polypeptide substrate may comprise one or more further amino acids at the N-terminus or the C-terminus or the N-terminus and the C-terminus of the polypeptide substrate.

Cleavage products of the SEQ ID NO: 1 or SEQ ID NO: 7 polypeptide substrate are also disclosed, particularly those cleavage products generated following fragmentation with ADAMTS13. In particular, C-terminal fragments are disclosed. Thus, in a further aspect there is provided an isolated polypeptide substrate for a disintegrin-like and metallopeptidase with thrombospondin type-1 motif, 13 (ADAMTS13) that is or is at least 52 (fifty two) amino acids in length and has an amino acid sequence that is substantially similar to part of the von Willebrand factor A2 domain sequence set forth in SEQ ID NO: 2, with one or more of the following modifications: (i) the amino acid corresponding to position 1610 of SEQ ID NO: 2 is mutated from N to C; and (ii) the amino acids corresponding to Q1624 to R1641 of SEQ ID NO: 2 are deleted. Suitably, the amino acid at the N-terminus of said polypeptide substrate corresponds to M1606 of SEQ ID NO: 2. Suitably, the amino acid at the C-terminus of said polypeptide substrate corresponds to R1668 of SEQ ID NO: 2. Suitably, said polypeptide is a synthetic polypeptide that comprises at least one portion of a detectable label. Suitably, at least one portion of the detectable label is a fluorophore or a quencher. Suitably, the attachment site for the fluorophore or the quencher is at the amino acid corresponding to position 1610 of SEQ ID NO: 2. In another aspect, there is provided an isolated polypeptide substrate for a disintegrin-like and metallopeptidase with thrombospondin type-1 motif, 13 (ADAMTS13) that is or is at least 45 (forty five) amino acids in length and has an amino acid sequence that is substantially similar to part of the von Willebrand factor A2 domain sequence set forth in SEQ ID NO: 2, with one or more of the following modifications: (i) the amino acid corresponding to position 1610 of SEQ ID NO: 2 is mutated from N to C; (ii) the amino acid corresponding to position 1629 of SEQ ID NO: 2 is mutated from G to E; and (iii) the amino acids corresponding to G1631 to R1641 of SEQ ID NO: 2 are deleted. Suitably, the amino acid at the N-terminus of said polypeptide substrate corresponds to M1606 of SEQ ID NO: 2. Suitably, the amino acid at the C-terminus of said polypeptide substrate corresponds to R1668 of SEQ ID NO: 2. Suitably, said polypeptide is a synthetic polypeptide that comprises at least one portion of a detectable label. Suitably, the at least one portion of the detectable label is a fluorophore or a quencher. Suitably, the attachment site for the fluorophore or the quencher is at the amino acid corresponding to position 1610 of SEQ ID NO: 2.

Isolated nucleotide sequences encoding the polypeptide substrates described herein are also disclosed. In addition, functional fragments of VWF genes are disclosed. Within the context of this disclosure, a "functional fragment" or "fragment" of a VWF gene refers to a nucleic acid molecule that encodes a portion of a VWF polypeptide which is a domain described herein or at least specifically interacts with ADAMTS13 as a substrate for the cleavage activity of ADAMTS13. A functional fragment of the VWF gene need not encode a polypeptide that contains each contiguous amino acid residue of the portion of VWF to which the functional fragment corresponds. In other words, the function fragment of VWF can align to a portion of native VWF and can include one or more of an insertion, a deletion or a substitution, so long as the functional fragment is a substrate to ADAMTS13 cleavage activity.

VWF is a large multimeric plasma glycoprotein crucial in the maintenance of hemostasis by functioning as both an antihemophilic factor carrier and a platelet-vessel wall mediator in the blood coagulation system, mainly by mediating tethering and adhesion of circulating platelets at sites of vascular injury. Mutations in this gene or deficiencies in this protein result in von Willebrand's disease (VWD).

VWF is expressed by endothelial cells and megakaryocytes. It is synthesized as 250-kDa monomers, which undergo intracellular processing, glycosylation, multimerization and propeptide removal that leads to formation of mature VWF multimers.

VWF multimeric size is modulated by the plasma metallopeptidase ADAMTS13 (a disintegrin and metallopeptidase with thrombospondin type I motif, member 13), which cleaves at a single site in the VWF A 2 domain (AA1498-1665; UniProtKB/Swiss-Pro database; Accession: P04275; FIG. 1) between Y1605 and M1606 (FIG. 2).

As described herein, a synthetic 55 (fifty five) amino acids (AA) in length polypeptide sequence designated as "GTI_FRET5" SEQ ID NO: 7 is disclosed, optionally modified with the insertion of a detectable label—such as a quencher and a fluorophore, that when recognized and cleaved by ADAMTS13 emits fluorescence. A synthetic 62 (sixty two) amino acids (AA) in length polypeptide sequence designated as "GTI_FRET4" SEQ ID NO: 1 is also disclosed, optionally modified with the insertion of a detectable label—such as a quencher and a fluorophore, that when recognized and cleaved by ADAMTS13 emits fluorescence.

Suitably, the polypeptide(s) are prepared using chemical synthesis techniques that are known in the art. The synthesis may utilize solid- or liquid-phase peptide synthesis. When modification of amino acid residues is required, modified amino acids can be introduced into a peptide synthesizer as appropriate.

It is also possible to produce the polypeptide substrates by recombinant procedures. Production of polypeptides by recombinant procedures can be carried out by methods well known to those skilled in the art, such as methods described by Sambrook, J., E. F. Fritsch, and T. Maniatis (1989, Molecular Cloning: A Laboratory Manual, Cold Spring Harbor Laboratory Press, Cold Spring Harbor, N.Y.).

Suitably, the polypeptide(s) can be lyophilized polypeptide(s). Lyophilization can be carried out according to procedures known to those skilled in the art, such as methods described in U.S. Pat. No. 5,556,771 and references therein.

The activity of ADAMTS13 in a subject can be measured using the polypeptide substrate for ADAMTS13. For example, the polypeptide substrate can be contacted with a sample from a subject—such as plasma—and the resultant polypeptide fragments of the polypeptide substrate are analysed. Various methods in the art can be used to analyse the resultant polypeptide fragments including the use of SDS-polyacrylamide gel electrophoresis. The proteins are stained using, for example, Coomassie Blue or silver staining or the like and the fragments produced are analysed. Alternatively, it may be possible to carry out Western blotting following the SDS-PAGE. Suitably, the results are compared with a control sample and/or a calibrator sample. The control sample may be or may be derived from a subject who is known to have 'normal' activity of ADAMTS13, such that a diagnosis of abnormal activity can be made.

Although the detectable label may be directly attached to an amino acid residue of a polypeptide, a detectable label may also be indirectly attached, for example, by being complexed with a chelating group that is attached (for example, linked via a covalent bond or indirectly linked) to an amino acid residue of the polypeptide. In a particular embodiment, the "detectable label" is any type of label that only substantially releases a detectable signal once the polypeptide substrate is cleaved. Thus, the detectable label may comprise a fluorescent resonance energy transfer (FRET) donor and/or acceptor. In one embodiment, the polypeptide substrate is modified by the incorporation or insertion of at least one quencher and at least one fluorophore, so that when recognized and cleaved by ADAMTS13 emits fluorescence. Suitably the substrate is a synthetic polypeptide (in contrast to a recombinant polypeptide) since this allows the direct incorporation of a quencher(s) and a fluorophore(s) therein. In the uncleaved substrate, fluorescence resonance energy transfer between the quencher and the fluorophore leads to low (for example, substantially no) fluorescence. Upon cleavage of the substrate by ADAMTS13, the quencher and fluorophore are separated which results in a detectable increase in fluorescence which can be measured.

Thus, in one embodiment, the polypeptide substrate includes a detectable label that allows the fragmentation of the polypeptide substrate to be measured directly. In one particular embodiment, the detectable label is a fluorophore and a quencher, wherein the quenching of the fluorophore is diminished as fragmentation occurs. Accordingly, fragmentation of the ADAMTS13 polypeptide substrate results in an increase in fluorescent signal. The cleavage of the substrate is detected by reading the fluorescence that results when the substrate is cleaved. According to the this embodiment of the invention, the skilled person will recognize that the polypeptide substrate will need to be synthesised by chemical synthesis techniques since recombinant approaches do not typically allow the incorporation of detectable labels therein.

The attachment site for the fluorophore and the quencher will typically be within the polypeptide substrate. Suitably, the fluorophore and the quencher will be separated from each other in such a manner that fluorescence from the fluorophore is substantially quenched when the polypeptide substrate is intact and fluorescence from the fluorophore is not quenched once the polypeptide substrate is cleaved. In one embodiment, the fluorophore and the quencher are separated by 8, 9, 10, 11 or 12 amino acids, suitably, the fluorophore and the quencher are separated by 9, 10, or 11 amino acids, more suitably, the fluorophore and the quencher are separated by 10 amino acids. In one embodiment, the attachment site for the fluorophore is at the amino acid corresponding to position 1610 of SEQ ID NO: 2 and/or the attachment site for the quencher is at the amino acid corresponding to position 1599 of SEQ ID NO: 2. It also contemplated that the positions of the fluorophore and quencher are reversed such that the quencher is at the amino acid corresponding to position 1610 of SEQ ID NO: 2 and/or the attachment site for the fluorophore is at the amino acid corresponding to position 1599 of SEQ ID NO: 2.

Another aspect relates to a method for measuring the activity of ADAMTS13 in a sample, which comprises contacting the polypeptide substrate described herein with a sample from a subject and analyzing the fragmentation products thereof.

There is also disclosed a kit or a diagnostic composition for in vitro testing of the ADAMTS13 activity in a subject (for example, a decrease or deficiency of ADAMTS13 activity) and therefore the presence of TTP or the predisposition to TTP, or for making a definitive diagnosis of TTP and a discrimination between TTP and HUS. Mild or moderately decreased levels of ADAMTS13 activity have also been associated with other disease states and conditions (see, for example, Kokame et al. Blood (2004) 103, 607; and Kokame et al. Br. J. Haematol (2005) 129, 93). The kit or the composition comprises a polypeptide substrate for ADAMTS13 as described herein. Typically, the kit will also include a one or more positive controls and/or one or more calibrators. Typically, the kit will also include a specimen diluent and/or a substrate buffer (for example, a buffer solution whose pH corresponds to a pH range of 5.8 to 6.7 that is suitable for in vitro testing of the proposed polypeptide substrates.). A set of instructions may also be provided. Methods for carrying out the in vitro testing of the ADAMTSI3 activity in a subject are known in the art (see e.g., Miyata, T., K. Kokame, F. Banno, Y. Shin, and M. Akiyama. 2007. ADAMTSI3 assays and ADAMTS13-deficient mice. *Curr. Opin. Hematol.* 14:277-283). Numerous vendors sell kits for detecting and/or determining the activity of ADAMTS-13 (see e.g., FRETS-VWF73 (Peptides International, U.S.A., Cat# SFR-3224-s), TECHNOZYM® ADAMTS-13 INH ELISA (Kordia, Netherlands, Cat# TC 5450401), Human ADAMTS13 ELISA Kit and ADAMTS13 Antibody Agarose Immobilized (both available from Bethyl Laboratories, U.S.A., Cat#s E88-500 and S300-391) and IMUBIND® ADAMTS13 ELISA (American Diagnostica, GmbH, Germany, Cat#813). Methods for collecting, transporting and processing blood specimens for coagulation testing and general performance of coagulation assays are known in the art (see for example, Approved Guideline H21-A4 NCCLS, Volume 23, Number 35, December 2003; Br. J. Haematol. 129:93-100 and Proc Natl Acad Sci USA. 2006; 103: 18470-4). The kit can also include an activator of ADAMTS13-such as divalent metal ions.

The polypeptide substrate may have a tag sequence attached at the N-terminus and/or at the C-terminus thereof. The tag sequence may be useful in the detection, quantification, or separation of cleaved products. Also, the tag sequence may be useful for immobilizing the polypeptide substrate onto a solid phase. Thus, the present invention also encompasses polypeptide substrates which are immobilized onto a solid phase using such tag sequences. The tag sequence can include, but are not limited to, proteins (for example, glutathione transferase, luciferase, beta-galactosidase), peptides (for example, His tags), coupling agents (for example, carbodiimide reagents), various kinds of labels (for example, radioactive labels, chromophores, and enzymes).

In further embodiments, the present invention relates to use of the polypeptide substrate for producing the diagnostic composition or the kit as described above.

The disclosure is further described in the Examples below, which are provided to describe the invention in further detail. These examples, which set forth a preferred mode presently contemplated for carrying out the invention, are intended to illustrate and not to limit the invention.

EXAMPLES

Example 1: Evaluation of SEQ ID NO: 1 Polypeptide Substrate (GTI_FRET4) as an ADAMTS13 Substrate Purpose:

The purpose of this experiment was to evaluate the polypeptide of SEQ ID NO: 1 (GTI FRET4; 62AA; MW 7855.9; polypeptide purity 95.5%) for use as an ADAMTS13 substrate in a second generation ADAMTS13 assay.

Synopsis of the Procedure:

The procedure in this example was performed substantially as described in Kokame, K., Y. Nobe, Y. Kokubo, A. Okayama, and T. Miyata. 2005. FRETS-VWF73, a first fluorogenic substrate for ADAMTS13 assay. *Br. J. Haematol.* 129:93-100, but using SEQ ID NO: 1 in place of the 73 amino acid substrate described therein. The FRETS-VWF73 substrate solution was dissolved in 25% dimethyl sulphoxide/water to prepare the 100 microM stock solution. The GTI FRET4 SEQ ID NO: 1 was dissolved in 100% DMSO. Both substrates were diluted to equal concentrations using ATS-13 substrate buffer (Gen-Probe GTI Diagnostics, Inc., U.S.A., Cat# ATS-13).

Plasma samples were diluted according to the ATS-13 Direction Insert using ATS-13 specimen diluent (Gen-Probe GTI Diagnostics, Inc., U.S.A., Cat# ATS-13). The diluted plasma samples were mixed with the diluted substrate and the fluorescence was read at 0, 5, 10, 15, 20, 30, 45 minutes using a Biotek FLX800 at the appropriate excitation and emission wavelengths for each substrate. The fluorescence values are reported in Table 1.

The fluorophore-quencher pair in the SEQ ID NO: 1 polypeptide substrate is FAM-5/TQ 2™ (Ex 485±20; Em 528±20; AAT Bioquest, Inc. Sunnyvale, Calif. U.S.A.). The fluorophore and quencher pair of FRETS-VWF73 (Nma/Dnp) described in Kokame has been substituted with FAM-5 and TQ_2 respectively in GTI_FRET4 SEQ ID NO: 1. Furthermore, in the SEQ ID NO: 1 polypeptide the position of the fluorophore (FAM-5) and quencher (TQ_2) has been swapped relative to the position of the fluorophore and quencher of the FRETS-VWF73 construct. Therefore, for GTI_FRET4 SEQ ID NO: 1, attachment of the fluorophore (FAM-5) occurs by substituting asparagine with cystine at position 15. The quencher (TQ_2) was attached by substituting glutamine with lysine at position 4 (FIG. 2 and Table 4).

Results:

The results of this experiment demonstrate that by using SEQ ID NO: 1 polypeptide substrate, as compared to the prior art FRETS-VWF73 substrate, a larger dynamic range is obtained. In this experiment, at 30 minutes there was approximately 34,000 Relative Fluorescence Units (RFU) difference between Calibrator A (equivalent to 0% of ADAMTS13 activity) and Calibrator E (equivalent to 100% of ADAMTS13 activity) compared to approximately 1500 to 2000 RFU difference for the FRETS-VWF73 substrate. See Table 1 and FIG. 3 and FIG. 4 for the change in fluorescence observed at all time points.

The calibration curves result in a linear trend line (see FIG. 4) compared to the FRETS-VWF73 assay which produces a calibration curve requiring a polynomial trend line (see FIG. 3). The calibration curve for the SEQ ID NO: 1 polypeptide substrate continued to be linear up through 45 minutes.

The % Normal (% N) activity (see Table 2) is calculated using the linear trend lines observed from the calibration curve at each time point. The % N ADAMTS13 activity calculated for each sample plateaus at 30 minutes and shows comparable results to FRETS-VWF73 after only 15 minutes.

Example 2: Direct Comparison of SEQ ID NO: 1 Polypeptide Substrate (GTI_FRET4) and the Prior Art FRETS-VWF73 Polypeptide Substrate (Peptides International; Louisville, Ky.)

Purpose:

The purpose of this experiment is to compare the SEQ ID NO: 1 polypeptide substrate to FRETS-VWF73 (SEQ ID NO: 6).

Synopsis of the Procedure:

For this experiment, substrate concentration and fluorescence reader settings determined on the previous experiment are used. The specimens tested (listed in Table 3), include a panel of proficiency samples prepared for use with ATS-13 (Gen-Probe GTI Diagnostics, Inc., U.S.A., Cat# ATS-13) which included samples with normal or deficient ADAMTS13 activity levels. In addition, six Factor Assay ConTrol plasma were used (2 FACT, 2 A-FACT and 2 B-FACT, from George King Biomedical Inc., Kansas, USA). The assays for the SEQ ID NO: 1 substrate and for the prior art FRETS-VWF73 assay were performed generally as according to the procedure described in Example 1. Substrate is prepared according to the conditions used for initial testing of the substrate, which prepared the molar amount of SEQ ID NO: 1 polypeptide substrate used in the assay to be equivalent to the molar amount of FRETS-VWF73 used in the prior art. The ELISA assays were read at 0, 5, 10, 15, 20, 30, 45 minutes.

Results

Figure 4:
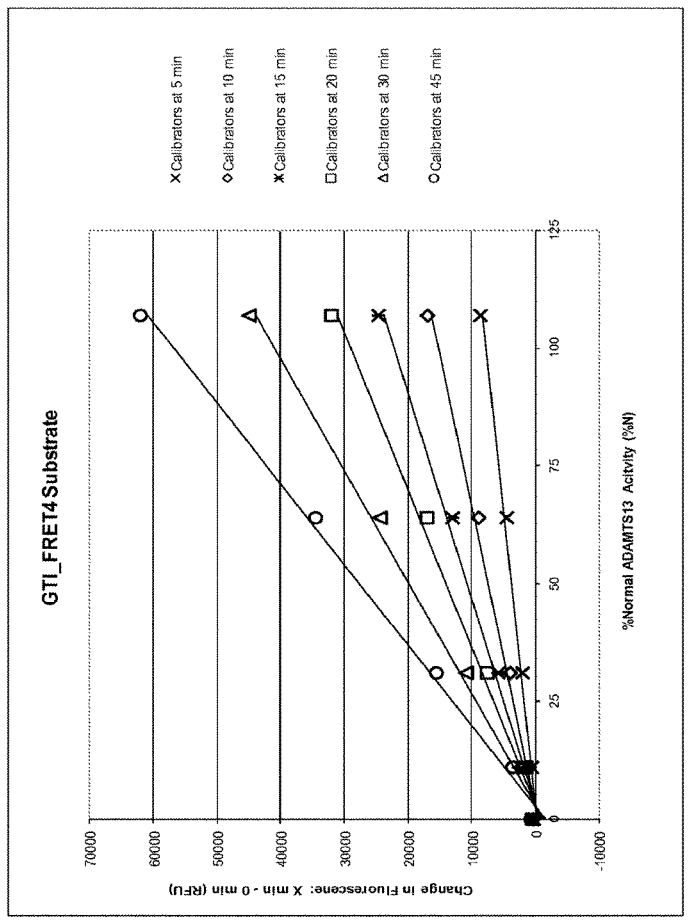
FIG. 4 displays a series of calibration curves obtained with Applicants synthetic 62 (sixty two) amino acids in length polypeptide sequence designated as "GTI_FRET4" SEQ ID NO: 1.

The results of these experiments confirm that the SEQ ID NO: 1 polypeptide substrate provides a much larger dynamic range compared to the FRETS-VWF73 substrate. At 30 minutes the difference between Calibrator A and E is approximately 35000 RFU compared to 2500 RFU observed for FRETS-VWF73 (FIGS. 3-4). The larger dynamic range would result in better sensitivity for samples with low ADAMTS13 activity. Moreover, when used at the same concentration as the FRETS-VWF73 substrate, the reaction time is faster. Consistent % N activity values are observed by the 15 minute reading (Table 2). The calibration curves are linear which would eliminate complicated analysis of results for the user.

Example 3: Evaluation of the Cleavage of SEQ ID NO: 7 Polypeptide Substrate (GTI_FRETS)

The purpose of this experiment is to compare the SEQ ID NO: 7 polypeptide substrate with the SEQ ID NO: 1 polypeptide substrate.

Synopsis of the Procedure:

Testing of substrate for cleavability by ADAMTS13 is determined as is generally described in Example 1.

Figure 5:
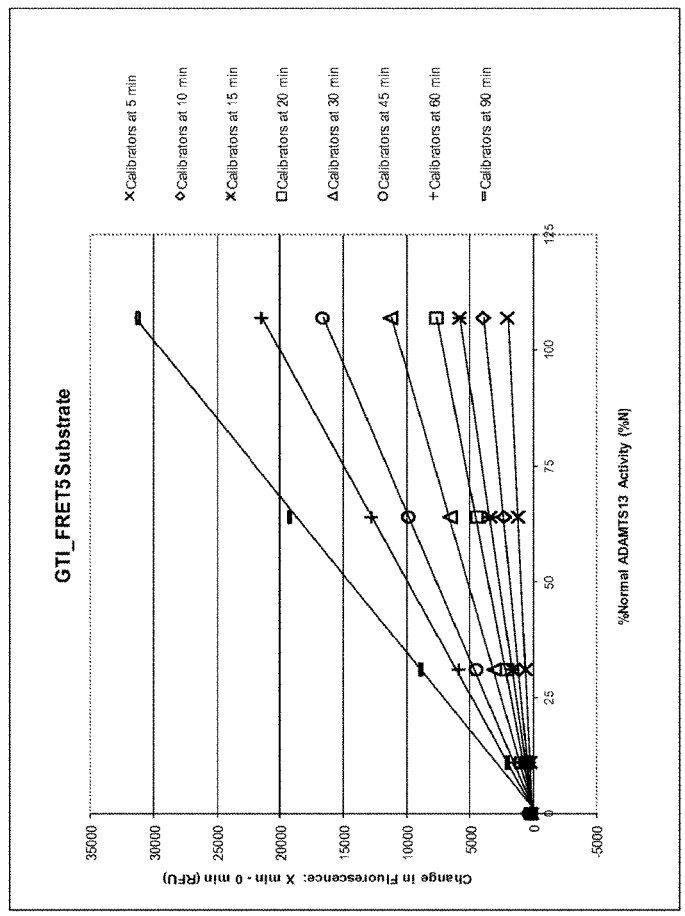
FIG. 5 displays a series of calibration curves obtained with Applicants synthetic 55 (fifty five) amino acids in length polypeptide sequence designated as "GTI_FRETS" SEQ ID NO: 7 Showing a change in fluorescence with time.

Results:

The change in fluorescence with time is shown in FIG. 5 and demonstrates that cleavage of the SEQ ID NO: 7 polypeptide substrate occurs.

Example 4: Evaluation of the Solubility of the SEQ ID NO: 7 Polypeptide Substrate and Assay Analysis The purpose of this experiment is to evaluate the solubility of the SEQ ID NO: 7 polypeptide substrate and to compare its performance with the SEQ ID NO: 1 polypeptide substrate.

250 .micro.L of working solution is prepared as above. The solution is vortexed vigorously and appears to be in solution. The solution is centrifuged at ~12,000 g for about 2 minutes. After centrifugation, a very small pink pellet is noted at the bottom of the tube. This suggests that at least some amount of the material precipitates. Another tube is prepared as above substituting water for the substrate buffer. This tube is also centrifuged. Once again a pink pellet is observed in the bottom of the tube. The pellet observed in the water solution is noticeably larger than the pellet observed in the substrate buffer solution. This suggests that the polypeptide is less soluble in water than in the buffer. The purpose of this experiment is to compare the SEQ ID NO: 7 GTI_FRETS polypeptide substrate to GTI_FRET4 (SEQ ID NO: 1). Testing of substrate for cleavability by ADAMTS13 is determined as is generally described in Example 1 but using GTI_FRETS instead of FRETS-VWF73.

The assay is read at 0, 5, 10, 15, 20, 30, 45, 60, and 90 minutes.

Results:

The data from this experiment demonstrates that the SEQ ID NO: 7 polypeptide substrate is not completely soluble in the working solution as prepared. However, the resulting calibration curve that is obtained is linear (see FIG. 5) and cleavage of the substrate occurs. A comparison of the activity obtained using SEQ ID NO: 1 polypeptide substrate or SEQ ID NO: 7 polypeptide substrate at 30 minutes post addition of substrate is shown in Table 5. The calibration curve for the SEQ ID NO: 7 polypeptide substrate continued to be linear up through 60 minutes.

Any publication cited or described herein provides relevant information disclosed prior to the filing date of the present application. Statements herein are not to be construed as an admission that the inventors are not entitled to antedate such disclosures. All publications mentioned in the above specification are herein incorporated by reference. Various modifications and variations of the disclosure will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled the art are intended to be within the scope of the following claims.

TABLE 1

Change in fluorescence observed using the SEQ ID NO: 1 peptide substrate
Increase in Fluorescence Values at Each Time Point (X minute-0 minute Reading)

| Sample ID | 15 min | 30 min | 45 min | 60 min | 75 min | 90 min |
|---|---|---|---|---|---|---|
| Calibrator A | 676 | 843 | 921 | 1,166 | 1,013 | 959 |
| Calibrator B | 1,765 | 3,000 | 4,164 | 5,358 | 6,468 | 7,581 |
| Calibrator C | 6,178 | 11,701 | 16,807 | 21,705 | 26,685 | 32,209 |
| Calibrator D | 10,887 | 20,626 | 29,206 | 37,289 | 44,543 | 53,613 |
| Calibrator E | 18,718 | 35,085 | 49,418 | 61,068 | 70,603 | 82,999 |
| Positive Control High | 9,146 | 17,281 | 24,859 | 31,857 | 39,838 | 47,473 |
| Positive Control Low | 2,182 | 3,902 | 5,511 | 7,169 | 8,789 | 10,370 |
| VF | 1,292 | 2,436 | 3,552 | 4,690 | 5,784 | 7,260 |
| UAMS041609 | 3,876 | 7,931 | 11,692 | 15,886 | 19,867 | 24,709 |
| MON110707 | 17,881 | 33,432 | 46,848 | 58,747 | 68,370 | 78,371 |

TABLE 2

Calculated % N activity using the linear trend line obtained for each time point using the SEQ ID NO: 1 peptide substrate

| | Assigned/Expected % Normal ADAMTS13 Activity Values Based on FRETS-VWF73 Substrate | % Normal ADAMTS13 Values Calculated Using GTI_FRET4 Substrate Incubation Time | | | | | |
|---|---|---|---|---|---|---|---|
| Sample ID | 30 Minutes | 15 Minutes | 30 Minutes | 45 Minutes | 60 Minutes | 75 Minutes | 90 Minutes |
| Calibrator A | 0 | 1 | 1 | 0 | 0 | 0 | 0 |
| Calibrator B | 9 | 7 | 7 | 7 | 7 | 6 | 6 |
| Calibrator C | 34 | 32 | 33 | 33 | 34 | 35 | 36 |
| Calibrator D | 55 | 58 | 59 | 59 | 60 | 61 | 62 |
| Calibrator E | 102 | 101 | 101 | 100 | 100 | 98 | 98 |
| Positive Control High | 36-54 | 48 | 49 | 50 | 51 | 54 | 55 |
| Positive Control Low | 6-17 | 10 | 10 | 10 | 10 | 10 | 9 |
| VF | ~20 | 5 | 6 | 6 | 6 | 5 | 6 |
| UAMS041609 | ~35 | 19 | 22 | 23 | 24 | 26 | 27 |
| MON110707 | ~90-100 | 97 | 96 | 95 | 96 | 95 | 92 |

TABLE 3

Materials used performing the examples

| Material | Manufacturer (Cat. No.) or Associated Date | Lot No. |
|---|---|---|
| ATS-13 Calibrators/Controls | GTI | CA-CE020410, PCH020410, PCL020410 |
| Substrate buffer (SBA) | GTI | SBA011810 |
| Specimen diluent (SDA) | GTI | SDA011810 |
| Substrate (SA) | GTI | SA112509 |
| Plate | GTI | ATS-011410 |
| DMSO | Sigma (D8418) | 038K07101 |
| Normal Pooled Plasma | GTI | NPP032206 |
| ATS-13 Proficiency Samples 1-5 | GTI | 020910-ATS |
| A-FACT plasma | George King BioMedical (A-FACT) | 1284 |
| A-FACT plasma | George King BioMedical (A-FACT) | 900 |
| B-FACT plasma | George King BioMedical (B-FACT) | 1114 |
| B-FACT plasma | George King BioMedical (B-FACT) | 1266 |
| FACT plasma | George King BioMedical (FACT) | 1223 |
| FACT plasma | George King BioMedical (FACT) | 222e1 |
| VF | Apr. 9, 2001 | Mar. 8, 2010 |
| BCM2 | Jul. 22, 2008 | Jul. 22, 2008 |
| UAMS041609 | Apr. 16, 2009 | Apr. 16, 2009 |
| ATS AC and AB CNTL | 05/14/209 | 2051008 |

TABLE 4

Amino acid sequences

| SEQ ID NO: | Sequence. N-terminus to C-Terminus. | note |
|---|---|---|
| 1 | DREKAPNLVYMTGCPASDEIKRLPGDIQVVPIEVIGWPNAPILIQDFETLP REAPDLVLQR | GTI FRET4 |
| 2 | MIPARFAGVLLALALILPGTLCAEGTRGRSSTARCSLFGSDFVNTFDGSMYS FAGYCSYLLAGGCQKRSFSIIGDFQNGKRVSLSVYLGEFFDIHLFVNGTVTQ GDQRVSMPYASKGLYLETEAGYYKLSGEAYGFVARIDGSGNFQVLLSDRYFN KTCGLCGNFNIFAEDDFMTQEGTLTSDPYDFANSWALSSGEQWCERASPPSS SCNISSGEMQKGLWEQCQLLKSTSVFARCHPLVDPEPFVALCEKTLCECAGG LECACPALLEYARTCAQEGMVLYGWTDHSACSPVCPAGMEYRQCVSPCARTC QSLHINEMCQERCVDGCSCPEGQLLDEGLCVESTECPCVHSGKRYPPGTSLS RDCNTCICRNSQWICSNEECPGECLVTGQSHFKSFDNRYFTFSGICQYLLAR DCQDHSFSIVIETVQCADDRDAVCTRSVTVRLPGLHNSLVKLKHGAGVAMDG QDVQLPLLKGDLRIQHTVTASVRLSYGEDLQMDWDGRGRLLVKLSPVYAGKT CGLCGNYNGNOGDDFLTPSGLAEPRVEDFGNAWKLHGDCODLQKOESDPCAL NPRMTRFSEEACAVLTSPTFEACHRAVSPLPYLRNCRYDVCSCSDGRECLCG ALASYAAACAGRGVRVAWREPGRCELNCPKGQVYLQCGTPCNLTCRSLSYPD EECNEACLEGCFCPPGLYMDERGDCVPKAQCPCYYDGEIFQPEDIFSDHHTM CYCEDGFMHCTMSGVPGSLLPDAVLSSPLSHRSKRSLSCRPPMVKLVCPADN LRAEGLECTKTCQNYDLECMSMGCVSGCLCPPGMVRHENRCVALERCPCFHQ GKEYAPGETVKIGCNTCVCODRKWNCTDHVCDATCSTIGMAHYLTEDGLKYL FPGECQYVLVQDYCGSNPGTFRILVGNKGCSHPSVKCKKRVTILVEGGEIEL FDGEVNVKRPMKDETHFEVVESGRYIILLLGKALSVVWDRHLSISVVLKQTY QEKVCGLCGNEDGIQNNDLTSSNLQVEEDPVDEGNSWKVSSQCADTRKVPLD SSPATCHNNIMKQTMVDSSCRILTSDVFQDCNKLVDPEPYLDVCIYDTCSCE SIGDCACFCDTIAAYAHVCAQHGKVVTWRTATLCPQSCEERNLRENGYECEW RYNSCAPACQVTCQHPEPLACPVQCVEGCHAHCPPGKILDELLQTCVDPEDC PVCEVAGRRFASGKKVTLNPSDPEHCQICHCDVVNLTCEACQEPGGLVVPPT DAPVSPTTLYVEDISEPPLHDFYCSRLLDLVELLDGSSRLSEAEFEVLKAFV VDMMERLRISQKWVRVAVVEYHDGSHAYIGLKDRKRPSELRRIASQVKYAGS QVASTSEVLKYTLFQIFSKIDRPEASRITLLLMASQEPQRMSRNFVRYVQGL KKKKVIVIPVGIGPHANLKQIRLIEKQAPENKAFVLSSVDELEQQRDEIVSY LCDLAPEAPPPTLPPDMAQVTVGPGLLGVSTLGPKRNSMVLDVAFVLEGSDK IGEADFNRSKEEMEEVIORMDVGODSIHVTVLOYSYMVTVEYPFSEAQSKGD ILQRVREIRYQGGNRTNTGLALRYLSDHSFLVSQGDREQAPNLVYMTGNPA SDEIKRLPGDIQVVPIGVGPNANVQELERIGWPNAPILIQDFETLPREAPDL VLQRCCSGEGLQIPTLSPAPDCSQPLDVILLLLDGSSSFPASYFDEMKSFAKA FISKANIGPRLTQVSVLQYGSITTIDVPWNVVPEKAHLLSLVDVMQREGGPS QIGDALGFAVRYLTSEMHGARPGASKAVVILVTDVSVDSVDAAADAARSNRV TVFPIGIGDRYDAAQLRILAGPAGDSNVVKLQRIEDLPTMVTLGNSFLHKLC SGFVRICMDEDGNEKRPGDVWTLPDQCHTVTCQPDGQTLLKSHRVNCDRGLR PSCPNSQSPVKVEETCGCRWTCPCVCTGSSTRHIVTFDGQNFKLTGSCSYVL FQNKEQDLEVILHNGACSPGARQGCMKSIEVKHSALSVELHSDMEVTVNGRL VSVPYVGGNMEVNVYGAIMHEVRFNHLGHIFTFTPQNNEFQLQLSPKTFASK TYGLCGICDENGANDFMLRDGTVTTDWKTLVQEWTVQRPGQTCQPILEEQCL VPDSSHCQVLLLPLFAECHKVLAPATFYAICQQDSCHQEVQCEVIASYAHLC RTNGVCVDWRTPDFCAMSCPPSLVYNHCEHGCPRHCDGNVSSCGDHPSEGCF CPPPDKVMLEGSCVPEEACTQCIGEDGVQHQFLEAWVPDHQPCQICTCLSGRK VNCTTQPCPTAKAPTCGLCEVARLRQNADQCCPEYECVCDPVSCDLPPVPHC ERGLQPTLTNPGECRPNFTCACRKEECKRVSPPSCPPHRLPTLRKTQCCDEY ECACNCVNSTVSCPLGYLASTATNDCGCTTTTCLPDKVCVHRSTIYPVGQFW EEGCDVCTCTDMEDAVMGLRVAQCSQKPCEDSCRSGFTYVLHEGECCGRCLP SACEVVTGSPRGDSQSSWKSVGSQWASPENPCLINECVRVKEEVFIQQRNVS CPQLEVPVCPSGFQLSCKTSACCPSCRCERMEACMLNGTVIGPGKTVMIDVC TTCRCMVQVGVISGFKLECRKTTCNPCPLGYKEENNTGECCGRCLPTACTIQ LRGGQIMTLKRDETLQDGCDTHFCKVNERGEYFWEKRVTGCPPFDEHKCLAE GGKIMKIPGTCCDTCEEPECNDITARLQYVKVGSCKSEVEVDIHYCQGKCAS KAMYSIDINDVQDQCSCCSPTRTEPMQVALHCTNGSVVYHEVLNAMECKCSP RKCSK | 1-22 Signal Peptide; 23-763 von willebrand antigen II; 764-2813 vwf. |
| 3 | MHQRHPRARCPPLCVAGILACGFLLGCWGPSHFQQSCLQALEPQAVSSYLSP GAPLKGRPPSPGFQRQRQRQRRAAGGILHLELLVAVGPDVFQAHQEDTERYV LTNLNIGAELLRDPSLGAQFRVHLVKMVILTEPEGAPNITANLTSSLLSVCG WSQTINPEDDTDPGHADLVLYITRFDLELPDGNRQVRGVTQLGGACSPTWSC LITEDTGFDLGVTIAHEIGHSFGLEHDGAPGSGCGPSGHVMASDGAAPRAGL AWSPCSRRQLLSLLSAGRARCVWDPPRPQPGSAGHPPDAQPGLYYSANEQCR VAFGPKAVACTFAREHLDMCQALSCHTDPLDQSSCSRLLVPLLDGTECGVEK WCSKGRCRSLVELTPIAAVHGRWSSWGPRSPCSRSCGGGVVTRRRQCNNPRP AFGGRACVGDADLQAEMCNTQACEKTQLEFMSQQCARTDGQPLRSSPGGASFY HWGAAVPHSQGDALCRHMCRAIGESFIMKRGDSFLDGTRCMPSGPREDGTLS LCVSGSCRTFGCDGRMDSQQVWDRCQVCGGDNSTCSPRKGSFTAGRAREYVT FLTVTPNLTSVYIANHRPLFTHLAVRIGGRYVAGKMSISPNTTYPSLLEDG RVEYRVALTEDRLPRLEEIRIWGPLQEDADIQVYRRYGEEYGNLTRPDITFT YFQPKPRQAWWWAAVRGPCSVSCGAGLRWVNYSCLDQARKELVETVQCQGSQ OPPAWPEACVLEPCPPYWAVGDFGPCSASCGGGLRERPVRCVEAQGSLLKTL | ADAMTS13 Isoform 1. 1-29 signal Peptide; 30-74 propeptide; 75-1427 ADAMTS13 chain. |

TABLE 4-continued

Amino acid sequences

| SEQ ID NO: | Sequence. N-terminus to C-Terminus. | note |
|---|---|---|
| | PPARCRAGAQQPAVALETCNPQPCPARWEVSEPSSCTSAGGAGLALENETCV PGADGLEAPVTEGPGSVDEKLPAPEPCVGMSCPPGWGHLDATSAGEKAPSPW GSIRTGAQAAHVWTPAAGSCSVSCGRGLMELRFLCMDSALRVPVQEELCGLA SKPGSRREVCQAVPCPARWQYKLAACSVSCGRGVVRRILYCARAHGEDDGEE ILLDTQCQGLPRPEPQEACSLEPCPPRWKVMSLGPCSASCGLGTARRSVACV QLDQGQDVEVDEAACAALVRPEASVPCLIADCTYRWHVGTWMECSVSCGDGI QRRRDTCLGPQAQAPVPADFCQHLPKPVTVRGCWAGPCVGQGTPSLVPHEEA AAPGRTTATPAGASLEWSQARGLLFSPAPQPRRLLPGPQENSVQSSACGRQH LEPTGTIDMRGPGQADCAVAIGRPLGEVVTLRVLESSLNCSAGDMLLLWGRL TWRKMCRKLLDMTFSSKTNTLVVRQRCGRPGGGVLLRYGSQLAPETFYRECD MQLFGPWGEIVSPSLSPATSNAGGCRLFINVAPHARIAIHALATNMGAGTEG ANASYILIRDTHSLRTTAFHGQQVLYWESESSQAEMEFSEGFLKAQASLRGQ YWTLQSWVPEMQDPQSWKGKEGT | |
| 4 | MHQRHPRARCPPLCVAGILACGFLLGCWGPSHFQQSCLQALEPQAVSSYLSP GAPLKGRPPSPGFQRQRQRQRRAAGGILHLELLVAVGPDVFQAHQEDTERYV LTNLNIGAELLRDPSLGAQFRVHLVKMVILTEPEGAPNITANLTSSLLSVCG WSQTINPEDDTDPGHADLVLYITRFDLELPDGNRQVRGVTQLGGACSPTWSC LITEDTGFDLGVTIAHEIGHSFGLEHDGAPGSGCGPSGHVMASDGAAPRAGL AWSPCSRRQLLSLLSAGRARCVWDPPRPQPGSAGHPPDAQPGLYYSANEQCR VAFGPKAVACTFAREHLDMCQALSCHTDPLDQSSCSRLLVPLLDGTECGVEK WCSKGRCRSLVELTPIAAVHGRWSSWGPRSPCSRSCGGGVVTRRRQCNNPRP AFGGRACVGADLQAEMCNTQACEKTQLEFMSQQCARTDGQPLRSSPGGASFY HWGAAVPHSQGDALCRHMCRAIGESFIMKRGDSFLDGTRCMPSGPREDGTLS LCVSGSCRTFGCDGRMDSQQVWDRCQVCGGDNSTCSPRKGSFTAGRAREYVT FLTVTPNLTSVYIANHRPLFTHLAVRIGGRYVVAGKMSISPNTTYPSLLEDG RVEYRVALTEDRLPRLEEIRIWGPLQEDADIQVYRRYGEEYGNLTRPDITFT YFQPKPRQAWVWAAVRGPCSVSCGAGLRWVNYSCLDQARKELVETVQCQGSQ OPPAWPEACVLEPCPPYWAVGDFGPCSASCGGGLRERPVRCVEAQGSLLKTL PPARCRAGAQQPAVALETCNPQPCPARWEVSEPSSCTSAGGAGLALENETCV PGADGLEAPVTEGPGSVDEKLPAPEPCVGMSCPPGWGHLDATSAGEKAPSPW GSIRTGAQAAHVWTPAAGSCSVSCGRGLMELRFLCMDSALRVPVQEELCGLA SKPGSRREVCQAVPCPARWQYKLAACSVSCGRGVVRRILYCARAHGEDDGEE ILLDTQCQGLPRPEPQEACSLEPCPPRWKVMSLGPCSASCGLGTARRSVACV QLDQGQDVEVDEAACAALVRPEASVPCLIADCTYRWHVGTWMECSVSCGDGI QRRRDTCLGPQAQAPVPADFCQHLPKPVTVRGCWAGPCVGQGACGRQHLEPT GTIDMRGPGQADCAVAIGRPLGEVVTLRVLESSLNCSAGDMLLLWGRLTWRK MCRKLLDMTFSSKTNTLVVRQRCGRPGGGVLLRYGSQLAPETFYRECDMQLF GPWGEIVSPSLSPATSNAGGCRLFINVAPHARIAIHALATNMGAGTEGANAS YILIRDTHSLRTTAFHGQQVLYWESESSQAEMEFSEGFLKAQASLRGQYWTL QSWVPEMQDPQSWKGKEGT | ADAMTS13 Isoform 2. |
| 5 | MHQRHPRARCPPLCVAGILACGFLLGCWGPSHFQQSCLQALEPQAVSSYLSP GAPLKGRPPSPGFQRQRQRQRRAAGGILHLELLVAVGPDVFQAHQEDTERYV LTNLNIGAELLRDPSLGAQFRVHLVKMVILTEPEGAPNITANLTSSLLSVCG WSQTINPEDDTDPGHADLVLYITRFDLELPDGNRQVRGVTQLGGACSPTWSC LITEDTGFDLGVTIAHEIGHSFGLEHDGAPGSGCGPSGHVMASDGAAPRAGL AWSPCSRRQLLSLLSANEQCRVAFGPKAVACTFAREHLDMCQALSCHTDPLD QSSCSRLLVPLLDGTECGVEKWCSKGRCRSLVELTPIAAVHGRWSSWGPRSP CSRSCGGGVVTRRRQCNNPRPAFGGRACVGADLQAEMCNTQACEKTQLEFMS QQCARTDGQPLRSSPGGASFYHWGAAVPHSQGDALCRHMCRAIGESFIMKRG DSFLDGTRCMPSGPREDGTLSLCVSGSCRTFGCDGRMDSQQVWDRCQVCGGD NSTCSPRKGSFTAGRAREYVTFLTVTPNLTSVYIANHRPLFTHLAVRIGGRY VVAGKMSISPNTTYPSLLEDGRVEYRVALTEDRLPRLEEIRIWGPLQEDADI QVYRRYGEEYGNLTRPDITFTYFQPKPRQAWVWAAVRGPCSVSCGAGLRWVN YSCLDQARKELVETVQCQGSQQPPAWPEACVLEPCPPYWAVGDFGPCSASCG GGLRERPVRCVEAQGSLLKTLPPARCRAGAQQPAVALETCNPQPCPARWEVS EPSSCTSAGGAGLALENETCVPGADGLEAPVTEGPGSVDEKLPAPEPCVGMS CPPGWGHLDATSAGEKAPSPWGSIRTGAQAAHVWTPAAGSCSVSCGRGLMEL RFLCMDSALRVPVQEELCGLASKPGSRREVCQAVPCPARWQYKLAACSVSCG RGVVRRILYCARAHGEDDGEEILLDTQCQGLPRPEPQEACSLEPCPPRWKVM SLGPCSASCGLGTARRSVACVQLDQGQDVEVDEAACAALVRPEASVPCLIAD CTYRWHVGTWMECSVSCGDGIQRRRDTCLGPQAQAPVPADFCQHLPKPVTVR GCWAGPCVGQGACGRQHLEPTGTIDMRGPGQADCAVAIGRPLGEVVTLRVLE SSLNCSAGDMLLLWGRLTWRKMCRKLLDMTFSSKTNTLVVRQRCGRPGGGVL LRYGSQLAPETFYRECDMQLFGPWGEIVSPSLSPATSNAGGCRLFINVAPHA RIAIHALATNMGAGTEGANASYILIRDTHSLRTTAFHGQQVLYWESESSQAE MEFSEGFLKAQASLRGQYWTLQSWVPEMQDPQSWKGKEGT | ADAMTS13 Isoform 3. |
| 6 | DREQAPNLVYMVTGNPASDEIKRLPGDIQVVPIGVGPNANVOELERIGWPNA PILIQDFETLPREAPDLVLQR | FRETS-VWF73 |

TABLE 4-continued

Amino acid sequences

| SEQ ID NO: | Sequence. N-terminus to C-Terminus. | note |
|---|---|---|
| 7 | DREKAPNLVYMVTGCPASDEIKRLPGDIIGWPNAPILIQDFETLPREAPDLV LQR | GTI FRETS |

TABLE 5

A comparison of the activity obtained using SEQ ID NO: 1 polypeptide substrate versus SEQ ID NO: 7 polypeptide substrate at 30 minutes post addition of substrate
% Normal ADAMTS13 Activity: 30 Minute Incubation Time

| Sample ID | GTI_FRET5 Substrate | GTI_FRET4 Substrate |
|---|---|---|
| Calibrator A | 3 | 4 |
| Calibrator B | 8 | 9 |
| Calibrator C | 30 | 29 |
| Calibrator D | 64 | 61 |
| Calibrator E | 108 | 110 |
| Positive Control High | 46 | 50 |
| Positive Control Low | 13 | 14 |
| 90 (ATS13-1) | 65 | 92 |
| 72 (ATS13-2) | 52 | 72 |
| 50 (ATS13-3) | 40 | 47 |
| 22 (ATS13-4) | 18 | 21 |
| 5 (ATS13-5) | 6 | 7 |
| UAMS041609 | 14 | 31 |
| BCM2 | 22 | 19 |
| VF040901 | 10 | 10 |
| CNTL | <Calibrator A | <Calibrator A |
| NPP032206 | 84 | >Calibrator E |
| NPP032206 HI | 12 | 9 |
| NPP032206 mixed | <Calibrator A | 57 |
| BCM2 HI | 15 | 12 |
| BCM2 mixed | 37 | 51 |
| CNTL HI | <Calibrator A | <Calibrator A |
| CNTL mixed | <Calibrator A | 4 |
| NPP032206 at 37 C. | 77 | 106 |
| A-FACT lot 1284 | <Calibrator A | 10 |
| A-FACT lot 900 | <Calibrator A | 10 |
| B-FACT lot 1114 | 28 | 45 |
| B-FACT lot 1266 | 23 | 46 |
| FACT lot 1223 | 82 | 107 |
| FACT lot 222e1 | 85 | 111 |

The invention claimed is:

1. An isolated polypeptide substrate for a disintegrin-like and metallopeptidase with thrombospondin type-1 motif, 13 (ADAMTS13), wherein said polypeptide substrate is from 45 to 70 amino acids in length and comprises:
   (a) the amino acid sequence set forth in SEQ ID NO:7; or
   (b) an amino acid sequence that is substantially similar to SEQ ID NO:7, wherein:
      (i) the amino acid corresponding to position 4 of SEQ ID NO:7 is lysine (K); and
      (ii) the amino acid corresponding to position 15 of SEQ ID NO:7 is cysteine (C).

2. The polypeptide substrate of claim 1 comprising the amino acid sequence set forth in SEQ ID NO:7.

3. The polypeptide substrate of claim 1, wherein said polypeptide substrate comprises a detectable label.

4. A kit comprising a polypeptide substrate of claim 1 and one or more calibrators containing a known concentration of ADAMTS13 activity and/or one or more positive controls for ADAMTS13 activity.

5. An isolated polypeptide substrate for a disintegrin-like and metallopeptidase with thrombospondin type-1 motif, 13 (ADAMTS13), wherein said polypeptide substrate is from 50 to 75 amino acids in length and comprises:
   (a) the amino acid sequence set forth in SEQ ID NO:1; or
   (b) an amino acid sequence that is substantially similar to SEQ ID NO:1, wherein:
      (i) the amino acid corresponding to position 4 of SEQ ID NO:1 is lysine (K);
      (ii) the amino acid corresponding to position 15 of SEQ ID NO:1 is cysteine (C); and
      (iii) the amino acid corresponding to position 34 of SEQ ID NO:1 is glutamic acid (E).

6. The polypeptide substrate of claim 5, wherein the amino acid at the N-terminus of said polypeptide substrate is aspartic acid (D).

7. The polypeptide substrate of claim 5, wherein the amino acid at the C-terminus of said polypeptide substrate is arginine (R).

8. The polypeptide substrate of claim 5, comprising the amino acid sequence set forth in SEQ ID NO:1.

9. The polypeptide substrate of claim 5, wherein said polypeptide substrate comprises a detectable label.

10. The polypeptide substrate of claim 9, wherein said detectable label comprises a fluorophore and a quencher.

11. The polypeptide substrate of claim 10, wherein:
  (i) said fluorophore is attached to cysteine (C) corresponding to position 15 of SEQ ID NO:1;
  and said quencher is attached to lysine (K) corresponding to position 4 of SEQ ID NO:1; or
  (ii) said quencher is attached to cysteine (C) corresponding to position 15 of SEQ ID NO:1; and
  said fluorophore is attached to lysine (K) corresponding position 4 of SEQ ID NO:1.

12. A method for measuring ADAMTS13 activity in a sample comprising: contacting said sample with a polypeptide substrate of claim 5.

13. The method of claim 12 wherein said measuring ADAMTS13 activity comprises detecting cleavage of said polypeptide substrate.

14. The method of claim 12, wherein said polypeptide substrate is attached to a solid support.

15. The method of claim 12, wherein said sample is a biological fluid or a tissue sample.

16. The method of claim 15, wherein said biological fluid is a blood sample or a plasma sample.

17. The method of claim 12, wherein said sample is obtained from a human subject.

18. A kit comprising a polypeptide substrate of claim 5 and one or more calibrators containing a known concentration of ADAMTS13 activity and/or one or more positive controls for ADAMTS13 activity.

19. The kit of claim 18 further comprising at least one of: a specimen diluent, a substrate buffer, and instructions for using said kit.

20. A method for cleaving a polypeptide comprising: contacting said polypeptide substrate of claim 5 with an ADAMTS13 protease.

* * * * *